United States Patent
Ominami et al.

(10) Patent No.: US 9,466,460 B2
(45) Date of Patent: Oct. 11, 2016

(54) CHARGED PARTICLE-BEAM DEVICE AND SPECIMEN OBSERVATION METHOD

(71) Applicant: Hitachi High-Technologies Corporation, Minato-ku, Tokyo (JP)

(72) Inventors: Yusuke Ominami, Tokyo (JP); Taku Sakazume, Tokyo (JP); Sukehiro Ito, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/891,494

(22) PCT Filed: Mar. 12, 2014

(86) PCT No.: PCT/JP2014/056392
§ 371 (c)(1),
(2) Date: Nov. 16, 2015

(87) PCT Pub. No.: WO2014/192361
PCT Pub. Date: Dec. 4, 2014

(65) Prior Publication Data
US 2016/0126058 A1 May 5, 2016

(30) Foreign Application Priority Data
May 30, 2013 (JP) ................................. 2013-113591

(51) Int. Cl.
*H01J 37/26* (2006.01)
*G01N 23/04* (2006.01)
(Continued)

(52) U.S. Cl.
CPC .............. *H01J 37/22* (2013.01); *G01N 23/046* (2013.01); *H01J 37/10* (2013.01); *H01J 37/20* (2013.01);
(Continued)

(58) Field of Classification Search
CPC .............................. H01J 37/00; G01N 23/046
USPC ......................................................... 250/311
See application file for complete search history.

(56) References Cited

U.S. PATENT DOCUMENTS 4,975,578 A * 12/1990 Tomimasu ............. G01N 23/04
250/307
(Continued)

FOREIGN PATENT DOCUMENTS

| JP | 55-32304 A | 3/1980 |
|---|---|---|
| JP | 4-337236 A | 11/1992 |

(Continued)

OTHER PUBLICATIONS

International Search Report (PCT/ISA/210) issued in counterpart International Application No. PCT/JP2014/056392 dated May 20, 2014, with English translation (Four (4) pages).
(Continued)

*Primary Examiner* — Robert Kim
*Assistant Examiner* — Eliza Osenbaugh-Stewar
(74) *Attorney, Agent, or Firm* — Crowell & Moring LLP

(57) ABSTRACT

An electron microscope has a large depth of focus in comparison with an optical microscope. Thus, information is superimposed on one image in the direction of depth. Therefore, it is necessary to accurately specify the three-dimensional position and density of a structure in a specimen so as to observe the three-dimensional structure of the interior of the specimen by using the electron microscope. Furthermore, a specimen that is observed with the optical microscope on a slide glass is not put into a TEM device of the related art. Thus, performing three-dimensional internal structure observation with the electron microscope on a location that is observed with the optical microscope requires very cumbersome preparation of the specimen. By controlling a vector parameter that defines the interrelationship between a primary charged particle beam and the specimen and by irradiation with the primary charged particle beam with a plurality of different vector parameters, images of transmitted charged particles of the specimen that correspond to each of the vector parameters are obtained. Irradiation with the primary charged particle beam is performed on the specimen that is arranged either directly or through a predetermined member on a detector which detects charged particles transmitted through or scattered by the interior of the specimen.

22 Claims, 16 Drawing Sheets

(51) Int. Cl.
  *H01J 37/22* (2006.01)
  *H01J 37/20* (2006.01)
  *H01J 37/244* (2006.01)
  *H01J 37/28* (2006.01)
  *H01J 37/10* (2006.01)

(52) U.S. Cl.
  CPC .............. *H01J 37/244* (2013.01); *H01J 37/26* (2013.01); *H01J 37/261* (2013.01); *H01J 37/28* (2013.01); *G01N 2223/3307* (2013.01); *G01N 2223/418* (2013.01); *H01J 2237/047* (2013.01); *H01J 2237/10* (2013.01); *H01J 2237/2802* (2013.01)

(56) References Cited

U.S. PATENT DOCUMENTS

| | | | |
|---|---|---|---|
| 5,051,585 A * | 9/1991 | Koshishiba | G03F 1/86 250/310 |
| 5,278,408 A | 1/1994 | Kakibayashi et al. | |
| 5,475,218 A | 12/1995 | Kakibayashi et al. | |
| 5,552,602 A | 9/1996 | Kakibayashi et al. | |
| 5,866,905 A * | 2/1999 | Kakibayashi | G01N 23/046 250/311 |
| 5,939,720 A | 8/1999 | Todokoro | |
| 6,051,834 A | 4/2000 | Kakibayashi et al. | |
| 6,963,069 B2 * | 11/2005 | Tanba | H01J 37/244 250/310 |
| 8,710,439 B2 | 4/2014 | Ominami et al. | |
| 8,921,786 B2 | 12/2014 | Ominami et al. | |
| 2009/0065708 A1 * | 3/2009 | Moon | G01N 23/046 250/440.11 |
| 2009/0166536 A1 | 7/2009 | Suga et al. | |
| 2014/0138542 A1 | 5/2014 | Inada et al. | |
| 2015/0076347 A1 | 3/2015 | Ominami et al. | |

FOREIGN PATENT DOCUMENTS

| | | |
|---|---|---|
| JP | 10-294074 A | 11/1998 |
| JP | 10-321176 A | 12/1998 |
| JP | 2008-84643 A | 4/2008 |
| JP | 2009-158222 A | 7/2009 |
| JP | 2013-25967 A | 2/2013 |
| WO | WO 2012/140822 A1 | 10/2012 |

OTHER PUBLICATIONS

Japanese language Written Opinion (PCT/ISA/237) issued in counterpart International Application No. PCT/JP2014/056392 dated May 20, 2014 (Five (5) pages).

* cited by examiner

Fig. 11A
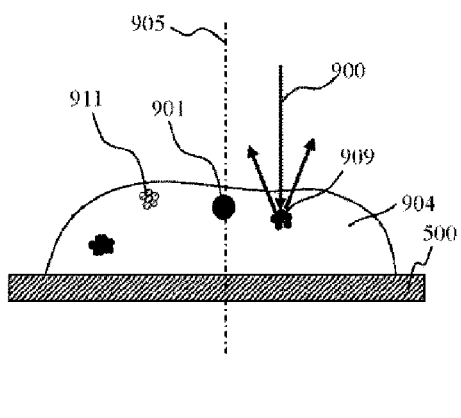
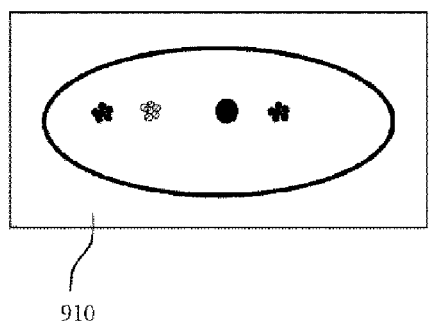
Fig. 11B
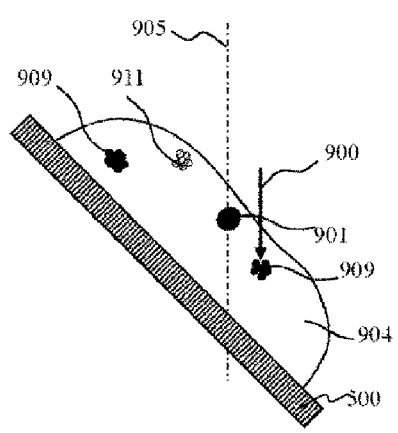
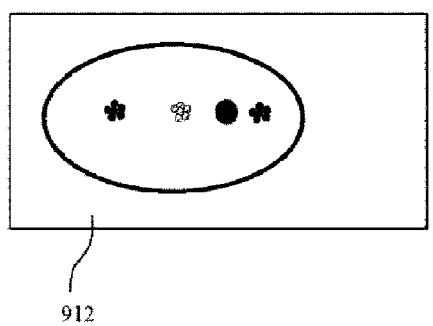

CHARGED PARTICLE-BEAM DEVICE AND SPECIMEN OBSERVATION METHOD

TECHNICAL FIELD

The present invention relates to a charged particle beam device and a specimen observation method capable of observing the interior of the specimen by irradiation with a charged particle beam.

BACKGROUND ART

A scanning transmission electron microscope (STEM), a transmission electron microscope (TEM), or the like is used to observe the internal structure of an object in a minute region. A known general method for observing the interior of a specimen by using such an electron microscope is arranging a specimen that is thinly sliced such that an electron beam can be transmitted therethrough on a specimen base on a mesh that is provided with multiple holes and obtaining a transmitted electron beam with a detector that is arranged on the opposite side of a specimen face from the source of electrons. Furthermore, a method of obtaining transmission electron microscope images in various directions by tilting the specimen has recently drawn attention in the field of materials science, medical science, and biology as a method for observation of the three-dimensional internal structure of an object. In PTL 1, there is suggested a method of finding a three-dimensional positional arrangement by tilting the specimen.

Not only an electron microscope, but also an optical microscope can be used to observe the internal structure of an object. By using an optical microscope, it is possible to obtain color information that cannot be obtained with an electron microscope. As a method for preparing a specimen for optical microscopic observation, wide use has been made of a method in which observation is performed by placing a specimen that is thin enough to allow transmission of light on a flat base such as a slide glass or by applying a liquid-state specimen onto the base or of such a method.

CITATION LIST

Patent Literature

PTL 1: JP-A-4-337236 (Specification of U.S. Pat. No. 5,278,408)

SUMMARY OF INVENTION

Technical Problem

Since the optical microscope has a small depth of focus, an optical microscope image has information of a specimen only within a specific depth or thickness. Thus, the three-dimensional internal structure of the specimen cannot be obtained even if the slide glass or the like is tilted. Meanwhile, the electron microscope has a large depth of focus in comparison with the optical microscope. Thus, information is superimposed on one image in the direction of depth. Therefore, in order to observe the three-dimensional structure of the interior of the specimen by using the electron microscope, it is necessary to accurately specify a structure having any size and density at a position inside the specimen in a three-dimensional direction.

It is necessary to introduce a specimen that is observed with the optical microscope into an electron microscope device capable of three-dimensional structure observation such as the one in PTL 1 when observing the three-dimensional structure of the interior of the specimen, which is observed with the optical microscope, with the electron microscope. However, the specimen that is mounted on the slide glass cannot be put into a TEM or STEM device such as the one in the literature of the related art. Thus, with the electron microscope, it is difficult to observe the three-dimensional internal structure of a location that is observed with the optical microscope. Although this can be realized by, for example, solidifying the specimen that is observed with the optical microscope on the flat base such as a slide glass with resin, separating the specimen from the flat base and thinly slicing with a microtome, and then arranging the thinly sliced specimen on a mesh that is provided with multiple holes, this work becomes a very cumbersome replacement of the specimen.

The present invention is devised with consideration of the problem, and an object thereof is to provide a charged particle beam device and a specimen observation method capable of accurately specifying the three-dimensional positional relationship and density distribution of the internal structure of the specimen by using an image of a transmitted charged particle beam.

Solution to Problem

In order to resolve the problem, in the present invention, by controlling a vector parameter that defines the interrelationship between a primary charged particle beam and a specimen and by irradiation with the primary charged particle beam with a plurality of different vector parameters, images of transmitted charged particles of the specimen that correspond to each of the vector parameters are obtained.

Furthermore, irradiation with the primary charged particle beam is performed on the specimen that is arranged either directly or through a predetermined member on a detector which detects charged particles transmitted through or scattered by the interior of the specimen.

Advantageous Effects of Invention

According to the present invention, it is possible to accurately specify the three-dimensional positional relationship and density distribution of the internal structure of a specimen by using an image of a transmitted charged particle beam.

Particularly, by using a specimen base that can detect a transmitted charged particle beam, the three-dimensional internal structure of the specimen that is observed with an optical microscope can be simply observed with a charged particle microscope device.

Problems, configurations, and effects other than those described above will become apparent from descriptions of embodiments below.

BRIEF DESCRIPTION OF DRAWINGS

FIGS. 11A and 11B are descriptive diagrams of a method for detecting transmitted charged particles with the detecting element.

DESCRIPTION OF EMBODIMENTS

Figure 1:
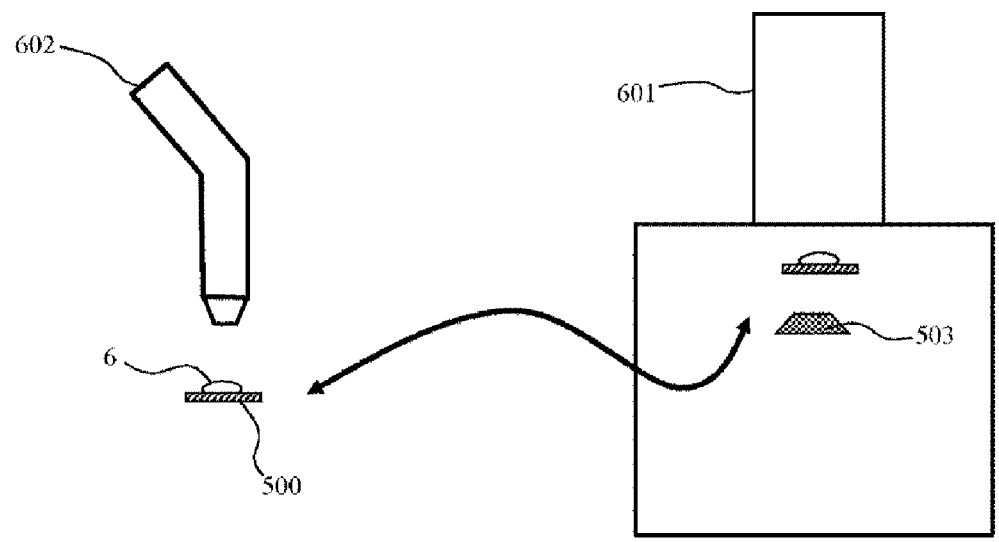
FIG. 1 is a schematic descriptive diagram of optical microscopic observation and charged particle beam microscopic observation.

Hereinafter, each embodiment will be described by using the drawings.

Hereinafter, details of a specimen base and a charged particle beam device to which the specimen base is applied in the present invention will be described. These are merely an example of the present invention. The present invention is not limited to the embodiments described below. The present invention can be applied to a device that observes a specimen by irradiation with a charged particle beam such as a scanning electron microscope, a scanning ion microscope, a scanning transmission electron microscope, and a transmission electron microscope, to a device that is configured of a combination of these microscopes and a specimen working device, or to an analyzing and inspecting device to which these microscopes are applied. The specimen base and the charged particle beam device in which the specimen base is mounted constitute an observation system that can observe an image of a transmitted charged particle beam.

The "specimen base" in the present description means a unit that can be detached along with a specimen from the charged particle beam device while the specimen is mounted thereon. Specifically, as described below, the "specimen base" unit may include a detecting element and a base or may be formed of only a detecting element.

First Embodiment

Summary

First, a summary of the specimen base used in the present embodiment will be described. While a method for observing a three-dimensional internal structure described below is also available with a general electron microscopic specimen base of the related art, using the below-described specimen base further improves convenience of use.

In the present embodiment, a charged particle microscope and an observation system that convert a charged particle beam which is transmitted through or scattered by the specimen into light and that generate an image of a transmitted charged particle beam by detecting the light will be described. More specifically, at least a part of the specimen base on which the specimen is mounted is formed of a light-emitting member that emits light by irradiation with a charged particle beam. Light is generated when the light-emitting member is irradiated with a charged particle beam that is transmitted through or scattered by the specimen on the light-emitting member. An image of a transmitted charged particle beam is generated by detecting the light with a detector that is provided in the charged particle microscope. That is, in the present embodiment, the charged particle beam that is transmitted through the specimen is not directly detected, but is detected after conversion into light. As described in detail below, the light-emitting member that converts a charged particle beam into light does not require interconnects such as a power supply cable and signal lines connected externally. Thus, the same specimen base can be used for observation in the charged particle beam microscope and in other devices, and very cumbersome work of disconnecting an electrical interconnect at the time of moving the specimen between devices becomes unnecessary. In addition, since the light-emitting member or the specimen base that includes the light-emitting member can be simply attached to and detached from the device, any type of specimen can be simply set on the specimen base. Particularly, this is very effective in the case of observing cultured cells where it is necessary to culture the specimen on the microscopic observational specimen base.

The same specimen base can be used for observation in the charged particle beam microscope and for observation in other devices such as an optical microscope when the specimen base of the present embodiment is used as illustrated in FIG. 1. FIG. 1 illustrates the specimen base, a charged particle beam microscope 601, and an optical microscope 602. The specimen base is provided with a detecting element 500 (also referred to as a light-emitting member) that can emit light by converting a charged particle beam into light or by amplifying the light in the present embodiment. A specimen 6 can be mounted on the detecting element 500 of the specimen base either directly or through a below-described predetermined member. As described below, a light detector 503 is provided in the charged particle beam microscope 601 so as to convert light from the detecting element 500 into an electrical signal and to amplify the electrical signal. According to this configuration, it is possible to obtain a transmission charged particle microscope image by detecting "charged particle transmission signal" that is transmitted through or scattered by the interior of the specimen after the specimen 6 is irradiated with a charged particle beam generated in the charged particle beam microscope. The detection is performed after the charged particle transmission signal is converted into light by the detecting element that constitutes a part of the specimen base. In addition, since the specimen base is a common specimen base that is used in common in the charged particle beam microscope and in the optical microscope, charged particle beam observation and optical observation are available while the specimen is arranged on one specimen base by moving the same specimen base between the microscopes during the observation as illustrated by an arrow in the drawing, without preparing a plurality of specimens for each microscopic observation or moving the specimen.

The detecting element that constitutes a part of the specimen base is favorably made of a transparent member in the present embodiment. Hereinafter in the present description, "transparent" means that visible light, ultraviolet light, or infrared light in a specific wavelength region can pass through or that visible light, ultraviolet light, or infrared light in all wavelength regions can pass through. Ultraviolet light has a wavelength region that includes wavelengths of approximately 10 nm to 400 nm. Visible light has a wavelength region that includes wavelengths of approximately 380 nm to 750 nm. Infrared light has a wavelength region that includes wavelengths of approximately 700 nm to 1 mm (=1000 μm). If, for example, the detecting element looks transparent although several colors are mixed therein, this means that visible light in a specific wavelength region can pass therethrough. If the detecting element is colorless and transparent, this means that visible light in all wavelength regions can pass therethrough. Here, the expression "can pass through" indicates the passage of light that has intensity such that optical microscopic observation is available with the light in at least the wavelength region (for example, a transmissivity of 50% or higher is desired). In addition, the specific wavelength region is a wavelength region that includes at least a wavelength region used in optical microscopic observation. Thus, the detecting element can be used in a general optical microscope (transmission optical microscope) that can detect "light transmission signal", which is obtained when light from one face side of the specimen base of the present embodiment is transmitted through the specimen, on the other face side of the specimen base. Any microscope that uses light such as a biological microscope, a stereoscopic microscope, an inverted microscope, a metallographical microscope, a fluorescence microscope, or a laser microscope may be used as the optical microscope. While "microscope" is referred to herein for description, the specimen base can be applied to general devices that obtain information by irradiation of the specimen with light, regardless of image magnifications.

When this specimen base is used, three-dimensional internal structure observation can be performed with the charged particle microscope device after the specimen arranged on the common specimen base is observed with the optical microscope. Thus, it is possible to obtain a variety of information from the same specimen on the same specimen base. Hereinafter, details of the specimen base, a method for mounting the specimen, a principle of obtaining an image, a configuration of a device, and the like will be described.

<Description of Specimen Base>

Figure 2:
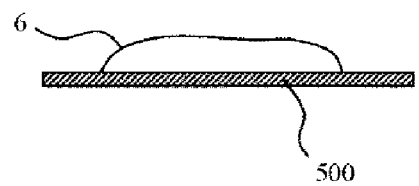
FIG. 2 is a detailed diagram of a specimen base that is provided with a detecting element.

Details and principles of the specimen base in the present embodiment will be described. The specimen base of the present embodiment is configured of the detecting element 500 that converts a charged particle beam into light. The specimen 6 is directly mounted on the detecting element 500 as illustrated in FIG. 2. While only one specimen 6 is mounted in the drawing, a plurality thereof may be arranged. Alternatively, the specimen 6 may be mounted indirectly through a member such as a film as described below. A base 501 (not illustrated) that is colorless and transparent or that has several colors mixed therein may be arranged under the specimen base 500. The base 501 includes transparent glass, transparent plastic, transparent crystal, or the like. When observation with a fluorescence microscope or the like is desired, plastic is favorable because fluorescence is not absorbed. The base 501 may not necessarily be provided.

The detecting element 500 is an element that detects a charged particle beam which approaches with an energy of, for example, approximately a few keV to a few tens of keV and that emits light such as visible light, ultraviolet light, or infrared light at the time of being irradiated with the charged particle beam. When the detecting element 500 is used in the specimen base of the present embodiment, the detecting element converts charged particles that are transmitted through or scattered by the interior of the specimen mounted on the specimen base into light. The wavelength of the emitted light may be in either a specific or an arbitrary wavelength region of visible light, ultraviolet light, and infrared light. As the detecting element, for example, a scintillator or a luminescent fluorescent material can be used. Examples of the scintillator include inorganic scintillator materials such as silicon nitride (SiN) and yttrium aluminum garnet (YAG) elements, an yttrium aluminum perovskite (YAP) element, a bismuth germanium oxide (BGO) element, a gadolinium silicon oxide (GSO) element, a lutetium silicon oxide (LSO) element, an yttrium silicon oxide (YSO) element, a lutetium yttrium silicon oxide (LYSO) element, and a thallium-activated sodium iodide (NaI(Tl)) element. Alternatively, a plastic scintillator that includes a material capable of emitting light such as polyethylene terephthalate, an organic scintillator, a material onto which a liquid scintillator that includes anthracene or the like is applied, or the like may also be used. The detecting element 500 may be made of any material provided that the detecting element 500 is an element capable of converting a charged particle beam into light.

A thin film or minute particles coated with a fluorescent agent that generates fluorescence when being irradiated with a charged particle beam may also be used. Examples of the coating material include fluorescent proteins such as a green fluorescent protein (GFP). The color of fluorescence is not limited to green and may be blue, red, or the like. Particularly, a GFP that is not instantly degraded even if being irradiated with a charged particle beam is favorable. Such a GFP is an enhanced green fluorescent protein (enhanced GFP, EGFP). When the specimen desired to be observed is a biological specimen such as a cell, the effect also achieved is good adhesion between the GFP which is a protein and the cell specimen. Observation may be performed after increasing the intensity of fluorescence of the GFP by irradiating a substrate onto which the GFP is applied with a charged particle beam after mounting the specimen thereon, or the specimen may be mounted after increasing the intensity of fluorescence of the GFP by irradiating the substrate with a charged particle beam before mounting the specimen thereon. In this case, the coating material is supported by or applied or sprayed onto the unillustrated transparent base 501. In the present embodiment, members that generate light when receiving charged particles on a light reception face including those described above will be collectively referred to as the light-emitting member. The inelastic mean free path of a charged particle beam depends on the accelerating voltage of the charged particle beam and ranges from a few tens of nm to a few tens of μm. Thus, a light emission region on the upper face of the detecting element 500 has approximately the same thickness from the surface of the detecting element. Therefore, the thickness of the detecting element 500 is favorably above this thickness. Meanwhile, as described above, in the case of considering performing optical microscopic observation with the same specimen base, since it is necessary to make a light transmission signal as transmittable as possible at the time of observation with the optical microscope, the detecting element in which several colors are mixed is favorably as thin as possible.

If the optical microscope 602 is a fluorescence microscope, it is necessary to inject fluorescent material into the specimen. In this case, it is desirable that the fluorescence wavelength band of the fluorescent material injected into the specimen and the light emission wavelength band of the fluorescent material as the light-emitting member of the present embodiment are shifted. For example, when the detecting element 500 is coated with a green fluorescent protein, it is desirable that the specimen is dyed with a red or blue fluorescent protein or the like. When the light-emitting member is coated in the same color as the dyed specimen, a difference in the intensity of light emission is favorably identified instead of color under the fluorescence microscope. When the fluorescent material is included in the specimen, the light detector 503 in the charged particle beam device detects light from the specimen base 500 and light from the specimen regardless of the color of the fluorescent material. In this case, if a detector that has a different ratio of amplification of the light emission wavelength is used in advance for the light detector 503, transmission information from charged particles can be obtained as a consequence. Specifically, if the light detector 503 used has a ratio of amplification of light from the light-emitting member that is greater than the ratio of amplification of light from the specimen, transmission signals from charged particles can be selectively amplified.

There are transparent specimen bases such as a slide glass (or a preparation) and a dish (or a Petri dish) that are widely used as the specimen base of the optical microscope. That is, when the specimen base 500 of the present embodiment that is provided with the detecting element capable of converting a charged particle beam into light is placed on the shape (for example, approximately 25 mm×approximately 75 mm×approximately 1.2 mm) of a general optical microscope slide glass, a user can operate the specimen base and mount and observe the specimen with the same experience level and sense as those that the user has exercised thus far. Alternatively, the specimen base may emit light by forming the specimen base such as a slide glass or a Petri dish of the above light-emitting member. Accordingly, it is possible to use a method in which specimens which are the target of observation with the optical microscope are primarily screened and in which the selected specimen is observed in detail with the charged particle microscope. In addition, since preparing the specimen requires a significant effort in a general high-performance transmission charged particle beam microscope device, observation with the specimen base of the present embodiment enables screening prior to observation with the high-performance transmission charged particle beam microscope. In addition, as described below, if positional information and the like are shared as a map on a computer or on a paper at the time of moving the specimen between these microscopes, it is possible to observe the same part in each microscope.

Figure 3A:
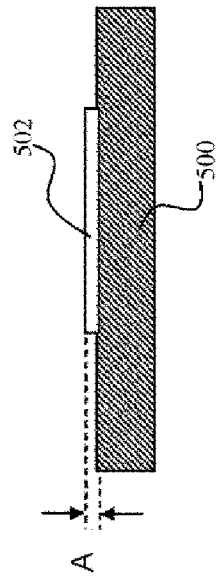
FIGS. 3A and 3B are detailed diagrams of the specimen base that is provided with the detecting element.
Figure 3B:
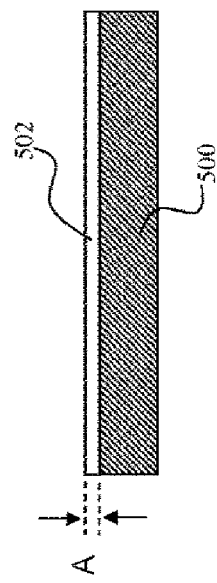

As described above, since the inelastic mean free path of a charged particle beam depends on the accelerating voltage of the charged particle beam and ranges from a few tens of nm to a few tens of μm, a film 502 that is thinner than the mean free path may be arranged between the detecting element 500 and the specimen. That is, the specimen is mounted on the thin film 502 that covers the detecting element 500. This specimen base is illustrated in FIG. 3 (*a*). The thickness of the specimen base is written as A in the drawing. The thin film 502 requires a thickness and a material that concurrently allow at least a part of a charged particle beam to be transmitted. Since optical microscopic observation is also performed, the thin film 502 requires more transparency with respect to light. If such a thin film 502 is arranged, it is possible to prevent staining, damage, or the like of the surface of the detecting element 500. As the thin film 502, a substance for increasing adhesion between the specimen and the specimen base may be applied onto the specimen base so that the specimen is not separated from the specimen base. For example, when the specimen is a biological specimen such as a cell, the surface of the cell is in a negatively charged state due to a lipid bilayer of a phospholipid. Thus, by applying positively charged molecules (lysine, aminosilane, or the like) onto the specimen base such as a slide glass, it is possible to prevent the separation of the cell specimen from the specimen base. Thus, positively charged molecules may be attached to the detecting element 500 in the same manner. Alternatively, a hydrophilic material may be applied so as to facilitate mounting of the specimen that includes a large amount of liquid. Alternatively, a biological specimen such as collagen and a highly hydrophilic material may be applied so as to facilitate mounting or culturing of living cells or germs. Here, applying includes a wide range of methods for attaching a coating material to the surface of the specimen, such as spraying, immersion, and coating. The molecules or the film may be arranged only at a predetermined position as illustrated in FIG. 3 (*b*). The predetermined position means a region of apart of the detecting element 500. For example, when the specimen is a biological specimen such as a cell, the specimen can be arranged only at the predetermined position by arranging positively charged molecules only at the predetermined position. This technique is useful when, for example, shortening observation time is desired by narrowing the region desired to be observed. A conductive member (anti-charging member) may be provided on at least the face where the specimen is mounted so that charging does not occur at the time of irradiation with a charged particle beam. The conductive member is, for example, a carbon material, a metal material, indium tin oxide (ITO), or a conductive organic substance. The number of layers in the film may be more than one.

Figure 4A:
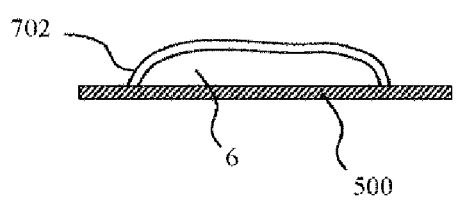
FIGS. 4A and 4B are detailed diagrams of the specimen base that is provided with the detecting element.
Figure 4B:
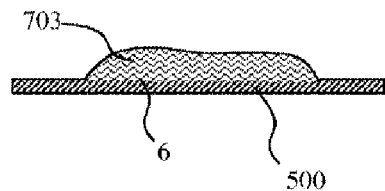

When the specimen is a hydrated specimen or the like, a thin film 702 may be arranged to surround or cover the observed specimen as illustrated in FIG. 4 (*a*). The thin film 702 is, for example, a surface-active material or an organic substance. By arranging the thin film 702 around the specimen, it is possible to prevent evaporation of water from the specimen or to prevent a change in the shape of the specimen. Alternatively, as illustrated in FIG. 4(*b*), a replacement substance 703 may be introduced into or around the specimen. The replacement substance 703 is, for example, an organic substance such as an ionic liquid. An ionic liquid has properties that can impart conductivity to the face which is irradiated with electrons. By arranging an ionic liquid in or around the observed specimen, it is possible to prevent the specimen from being charged when the specimen is irradiated with a charged beam particle in a vacuum. Furthermore, by replacing the ionic liquid with water in the specimen, it is possible to maintain the form of the specimen. Thus, it is possible to obtain a transmission image of a wetter specimen by detecting emission of light due to a charged particle beam that is transmitted through or scattered by the specimen which includes the ionic liquid. A method for placing the ionic liquid on the specimen may be immersing the specimen in the ionic liquid or may be blowing the ionic liquid on the specimen with a spray or the like.

Figure 5:
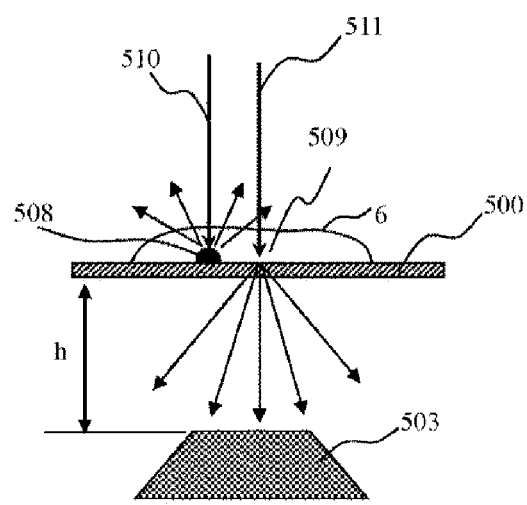
FIG. 5 is a descriptive diagram of a method for detecting transmitted charged particles with the detecting element.

Hereinafter, a method for detecting light by using the specimen base of the present embodiment and a principle in which a transmitted charged particle beam can be obtained will be described. FIG. 5 illustrates a state where the specimen 6 is arranged on the detecting element 500. The light detector 503 is illustrated under the specimen base. The light detector 503 can convert a light signal from the detecting element 500 into an electrical signal or can amplify the electrical signal. The converted or amplified electrical signal is input into a control unit or into a computer through a communication line and is formed into an image by these control systems. The obtained image (image of a transmitted charged particle beam) may be displayed on a monitor or the like.

It is considered that there are a high-density part 508 and a low-density part 509 in the specimen. When the high-density part 508 of the specimen is irradiated with a primary charged particle beam 510, the charged particle beam is mostly backscattered. Thus, the charged particle beam does not reach the detecting element 500. Meanwhile, when the low-density part 509 of the specimen is irradiated with the primary charged particle beam 511, the charged particle beam can be transmitted to the detecting element 500. As a consequence, it is possible to detect (that is, to convert into a light signal) a density difference in the specimen with the detecting element 500. This state of transmission changes depending on the acceleration energy of the charged particle beam. Thus, by changing the acceleration energy of the charged particle beam, the density of the internal structure of the specimen that is formed into an image can be selected. That is, it is possible to change the interior information desired to be observed and the region thereof. In addition, the diameter of the beam can be changed by changing the amount of the beam current of the charged particle beam. As a consequence, it is possible to change the relative size between the size of the internal structure observed and the diameter of the beam. That is, by changing the beam current, it is possible to make the interior information desired to be observed either visible or invisible.

While there may be a space between the light detector 503 and the specimen base (part designated by h in the drawing), the light transmission part h is favorably as short as possible so as to detect light as efficiently as possible. Alternatively, an optical lens, a mirror, or the like may be arranged in the light transmission part h to concentrate light. The light transmission part h may be in the air or in a vacuum. A solid material that can allow light in the emission wavelength region to pass therethrough is a material that is transparent or semi-transparent with respect to light, such as quartz, glass, an optic fiber, or plastic. If this configuration is used, the light detector 503 can be arranged separately from a stage. Thus, it is possible to arrange interconnects or electric circuits connected to the light detector 503 at a position separated from the specimen base and from the specimen stage that retains the specimen base. In any case, the light transmission part h is required to be capable of allowing passage of light in the emission wavelength region as much as possible. While the light detector 503 is arranged under the specimen base 500 in FIG. 5, the light detector 503 may be arranged horizontally with or above the specimen base 500 or may be at any position provided that the light detector 503 can obtain light from the detecting element 500.

A method for mounting the specimen on the specimen base will be described below. The specimen is required to be thin because the charged particle beam (furthermore, light in the case of also performing optical microscopic observation) has to be transmitted therethrough. For example, the thickness of the specimen ranges from approximately a few nm to a few tens of µm. Examples of a specimen that can be directly mounted on the detecting element 500 include a liquid or mucous membrane that includes cells, a liquid biological sample such as blood or urine, a sliced cell, particles in a liquid, minute particles such as germs, fungi, or viruses, and a soft material that includes minute particles, organic substances, or the like. As a method for mounting the specimen, the following method is considered in addition to the culturing. For example, there is a method in which the specimen is dispersed in a liquid and in which the liquid is attached to the detecting element. The specimen may be sliced at a thickness that allows the charged particle beam to be transmitted, and the sliced specimen may be arranged on the detecting element. More specifically, for example, the specimen may be attached to the tip end of a cotton swab and be applied onto the detector or may be dropped by using a pipette. When the specimen is minute particles, the specimen may be scattered over the detector. The specimen may be applied by using a spray or the like. Spin coating in which a liquid is applied onto the specimen base through high-speed rotation may also be used. Dip coating in which a liquid is applied onto the specimen base by immersing the specimen base in the liquid and by pulling the specimen base up may also be used. Any of these methods may be used provided that the thickness of the specimen can be a thickness ranging from a few tens of nm to a few tens of µm.

<Description of Principle of Three-Dimensional Internal Structure Observation>

Next, a principle for observing the three-dimensional internal structure of the specimen by using a charged particle beam will be described by using FIG. 6. The drawing illustrates the interrelationship between the specimen 6 and irradiation with a charged particle beam 900. A substance 904 that has comparatively low density in the specimen 6 includes an internal substance 901, an internal substance 902, and an internal substance 903 that have comparatively high density. The internal substance 903 has a small size and low density in comparison with the internal substances 901 and 902. When, for example, a cell specimen is considered as the specimen, the substance 904 corresponds to the interior of the cell, and the internal substances 901, 902, 903, and the like correspond to the cell organelles and the like of the cell nucleus or the like.

It is assumed that an optical axis 905 that is the axis of a charged particle optical lens tube is in the vertical direction of the drawing. It is considered that the specimen 6 is irradiated with the charged particle beam 900 and is scanned in the left-right direction on the page of the drawing and that, in turn, a signal that is a light signal converted by the detecting element 500 is displayed on a monitor as a microscope image. Since the internal substances 901 and 902 have high density in FIG. 6(a), most of the incident charged particle beam 900 is backscattered while some amount of the charged particle beam passes through the internal substance 903 which has low density. As a consequence, the image that is detected under the specimen after scanning with the charged particle beam looks like a projected image (or a detected image or a transmitted charged particle image) 906. For example, the distance between the internal substance 901 and the internal substance 902 in the projected image 906 is not the actual distance therebetween and is a distance C that is projected from above. Most of the charged particle beam passes through the internal substance 903 and cannot be detected. Thus, the internal substance 903 does not appear in the projected image 906.

Figure 6A:
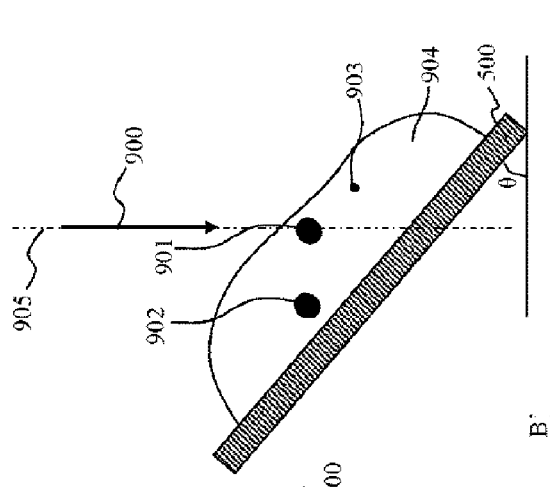
FIGS. 6A-6C are descriptive diagrams of a method for detecting transmitted charged particles with the detecting element.

Next, FIG. 6 (b) is a descriptive diagram in a case where an incident energy E of the charged particle beam 900 is decreased from that in FIG. 6(a) and is a projected image obtained in that case. The magnitude of the incident energy E is explicitly illustrated by the thickness of the arrows in the drawing. If the incident energy E is small, the amount of the charged particle beam that is backscattered without being able to pass through even the internal substance 903 increases. Thus, an internal structure 903a is detected in addition to the structures of the internal substances 901 and 902 in a projected image (or a detected image) 907. This is due to a phenomenon in which a charged particle beam having a lower energy is likely to be scattered by substances.

Figure 6B:
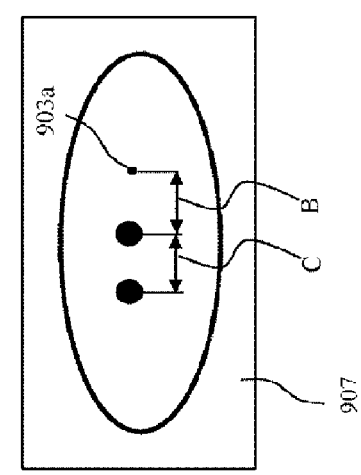
Figure 6C:
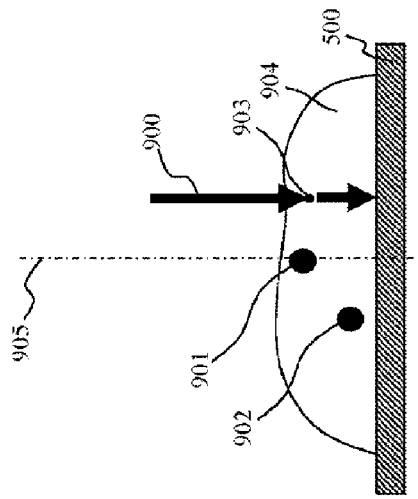

The three-dimensional positional relationship among the internal substance 901, the internal substance 902, and the internal substance 903 is not clear in the projected images obtained in FIG. 6(a) and FIG. 6(b). Therefore, a plurality of projected images is obtained by changing the relative angle between the direction of incidence of the charged particle beam and the specimen. Specifically, either the specimen is tilted or the incidence of the charged particle beam is tilted with respect to the optical axis 905. On the basis of the plurality of projected images, it is possible to obtain the three-dimensional positional arrangement of the internal structure. FIG. 6(c) illustrates a state where the specimen 6 is irradiated with a slantwise charged particle beam by tilting the specimen base 500 at θ. When the projected image 907 is compared with a projected image (or a detected image) 908, the distances among the internal substance 901, the internal substance 902, and the internal substance 903 are changed (parts C' and D' in the drawing). Furthermore, the size of the substance 904 is also changed (part B' in the drawing). That is, by finding the amount of change after comparing and observing the projected image 907 and the projected image 908, it is possible to observe the three-dimensional internal structure of the entirety and interior of the specimen 6.

Although illustration is not provided, the diameter of the beam can be changed by changing a beam current amount I of the charged particle beam. As a consequence, it is possible to change the relative size between the size of the internal structure observed and the diameter of the beam. That is, by changing the beam current, it is possible to make the interior information desired to be observed either visible or invisible. That is, the beam current amount I of the charged particle beam may be set as a vector parameter so as to separate information which is desired to be seen from information which is not desired to be seen.

To sum up the above description, the important factors for performing three-dimensional internal structure observation are the relative irradiation angle θ, the energy E of the charged particle beam, and the beam current amount I of the charged particle beam at the time of irradiation of the specimen with the charged particle beam. These are collectively the vector of the charged particle beam. In the present description, the relative irradiation angle θ between the direction of incidence of the primary charged particle beam and the specimen, the incident energy E of the primary charged particle beam, and the beam current amount I of the charged particle beam are collectively referred to as a vector parameter. That is, the vector parameter means a parameter that defines the interrelationship between the primary charged particle beam and the specimen. That is, by controlling the irradiation angle θ, the energy E of the charged particle beam, and the beam current amount I of the charged particle beam that define a vector, the internal structure of the specimen on the specimen base 500 can be observed on the basis of a plurality of images that is obtained by irradiation with the primary charged particle beam under conditions of different vector parameters. The plurality of images is images of the transmitted charged particles that correspond to each vector parameter. It is possible to identify how the three-dimensional internal structure is formed by obtaining the plurality of images after changing the irradiation angle θ, the energy E of the charged particle beam, and the beam current amount I of the charged particle beam of the vector parameter and by either observing all of these images or displaying the images continuously. In addition, the three-dimensional internal structure can be quantified by comparing several images after measuring sizes such as the distance and area of the internal structure. Hereinafter, "changing the vector parameter" means changing or controlling at least one of the relative irradiation angle θ between the direction of incidence of the primary charged particle beam and the specimen, the energy E of the primary charged particle beam, and the beam current amount I of the charged particle beam.

It may be desirable to obtain the interior information in a prompt manner and in real time. For example, as described below, this is when the specimen is automatically moved and is represented as a tomogram by a computed tomography (CT). In this case, the period of time during which the specimen base is arranged in the charged particle beam device is limited. In such a case, the irradiation angle θ, the energy E of the charged particle beam, and the beam current amount I of the charged particle beam may be changed as a set in a real-time manner. As a consequence, the interior information desired to be seen can be observed more promptly.

<Description of Device>

A device capable of performing three-dimensional internal structure observation by mounting the specimen base of the present embodiment therein will be described with reference to FIG. 7. The charged particle microscope is mainly configured of a charged particle optical lens tube 2, a casing 7 (hereinafter, may be referred to as a vacuum chamber) that supports the charged particle optical lens tube with respect to the face on which the device is installed, and a control system that controls these. The air inside the charged particle optical lens tube 2 and inside the casing 7 is exhausted therefrom to make a vacuum by a vacuum pump 4 at the time of use of the charged particle microscope. Operations for launching and stopping the vacuum pump 4 are also controlled by the control system. While only one vacuum pump 4 is illustrated in the drawing, the vacuum pump 4 may be provided in quantities of two or more.

The charged particle optical lens tube 2 is configured of elements such as a charged particle source 8 that generates the primary charged particle beam and an optical lens 1 that concentrates and guides the generated charged particle beam to the lower portion of the lens tube and that scans the primary charged particle beam over the specimen 6. The charged particle optical lens tube 2 is installed to protrude into the casing 7 and is fixed to the casing 7 through a vacuum seal member 123. A detector 3 that detects secondary charged particles (secondary electrons, reflective electrons, or the like) obtained by irradiation with the primary charged particle beam is arranged in an end portion of the charged particle optical lens tube 2. The detector 3 may be at any position other than the illustrated position provided that the detector 3 is inside the casing 7.

Transmitted charged particles or secondary charged particles such as reflective charged particles are emitted from the interior or surface of the specimen by the charged particle beam that reaches the specimen 6. The secondary charged particles are detected by the detector 3. The detector 3 is a detecting element that can detect and amplify the charged particle beam which approaches with an energy of a few keV to a few tens of keV. The detector 3 is, for example, a semiconductor detector that is made of a semiconductor material such as silicon or is a scintillator that can convert a charged particle signal into light on the glass face or in the interior thereof.

A vacuum pipe 16 having one end connected to the vacuum pump 4 is connected to the casing 7 so that a vacuum state can be maintained in the interior of the casing 7. In addition, a leak valve 14 for releasing the interior of the casing to the atmosphere is provided so that the interior of the casing 7 can be released to the atmosphere when the specimen base is introduced into the device. The leak valve 14 may not be provided or may be provided in quantities of two or more. The location where the leak valve 14 is arranged in the casing 7 is not limited to the location illustrated in FIG. 7. The leak valve 14 may be arranged at other positions on the casing 7.

The casing 7 is provided with an opening portion on a side face thereof. The opening portion includes a lid member 122 and a vacuum seal member 124 that airtightly maintain the vacuum in the device. The charged particle microscope of the present embodiment is provided with a specimen stage 5 so as to change the positional relationship between the specimen and the charged particle optical lens tube after the specimen mounted on the specimen base is put into the casing 7 as described above. The light-emitting member or the specimen base that includes the light-emitting member is arranged in the specimen stage 5 in an attachable and detachable manner. A supportive plate 107 that serves as a bottom plate supported by the lid member 122 is installed, and the stage 5 is fixed to the supportive plate 107. The stage 5 is provided with an XYZ drive mechanism for movement in an in-plane direction or in a heightwise direction and with a tilted drive mechanism that can tilt the specimen with respect to an optical axis 200 of the charged particle optical lens tube. The stage 5 may be further provided with a rotational drive mechanism that can rotate about the optical axis. The supportive plate 107 is installed to extend toward the inside of the casing 7 facing a face of the lid member 122. Supportive shafts extend from each of a number of drive mechanisms of the stage 5 and are respectively connected to a drive unit 51 and a drive unit 52 that the lid member 122 includes. While only two drive units are illustrated in the drawing, the drive unit is arranged in quantities corresponding to the number of drive mechanisms. The drive unit 51 and the drive unit 52 are electric motors. The drive unit 51 and the drive unit 52 may be rotated manually by the user. The user of the device can adjust the position of the specimen by operating the drive units 51 and 52 manually or by inputting an instruction directed to a higher control unit using a user interface 34. In addition, although illustration is not provided, the optical microscope may be provided in the casing 7.

The detecting element 500 on which the specimen is mounted can be mounted on the specimen stage 5. As described above, the detecting element 500 converts the charged particle beam into light. The light detector 503 for detecting and converting the light into an electrical signal and amplifying the signal is provided on the specimen stage 5 or near the stage. As described above, it is desirable that these elements are arranged so that a light signal can be efficiently detected. For example, the light detector and the specimen base provided with the detecting element 500 may be present nearby or may be in contact or not in contact. Alternatively, the light transmission part h may be arranged between these. While the light detector is provided in the specimen stage in the drawing, the light detector 503 may be fixed to anywhere in the casing 7 to detect emission of light from the specimen base 500. The light detector 503 may be installed outside the casing 7, in which case light is guided and detected outside the casing 7. When the light detector 503 is outside the casing 7, the light detector can detect a signal by providing a light transmission path such as glass or an optical fiber for transmission of light near the specimen base 500 so that a light signal converted by the detecting element 500 is transmitted through the light transmission path. The light detector 503 is, for example, a semiconductor detecting element or a photomultiplier. In any case, the light detector of the present embodiment detects light that is emitted by the detecting element of the specimen base.

The drawing illustrates a state where the light detector 503 is provided in the upper portion of the stage 5. A preamplifier substrate 505 is connected via an interconnect 509 to the light detector 503 provided in the stage 5. The preamplifier substrate 505 is connected to a lower control unit 37 via an interconnect 507 or the like. While the preamplifier substrate 505 is inside the casing 7 in the drawing, the preamplifier substrate 505 may be outside the casing 7 (for example, at the preamplifier 54 part in the drawing). As described below, it is necessary to prevent the specimen base 500 from falling from the specimen stage 5 at the time of tilting the specimen base 500. Thus, a fixing member 506 that can define a position to arrange the specimen base 500 on the specimen stage 5 is provided. In addition, an unillustrated fixing member may be provided between the specimen base 500 and the light detecting element 503. Accordingly, it is possible to fix the specimen base 500 and to prevent positional shifting.

The charged particle beam device of the present embodiment includes both of the detector 3 and the detecting element 500. Thus, secondary charged particles emitted from or reflected by the specimen can be obtained by the detector 3, and in addition, transmitted charged particles transmitted through or scattered by the specimen can be obtained by the detecting element 500. Therefore, it is possible to switch display of an image of the secondary charged particle beam and an image of the transmitted charged particles on a monitor 35 by using the lower control unit 37 and the like. In addition, it is also possible to display the two types of images at the same time.

The control system of the charged particle microscope of the present embodiment is provided with a higher control unit 36, the lower control unit 37, and a stage control unit 38. The higher control unit 36 is connected to the user interface 34 such as a keyboard or a mouse used by the user of the device and to the monitor 35 on which the microscope image is displayed and communicates therewith. The lower control unit 37 controls a vacuum exhaust system, a charged particle optical system, and the like according to an instruction transmitted from the higher control unit 36. The stage control unit 38 transmits and receives signals with the drive unit 51 and the drive unit 52. The units are connected to each other by a communication line. The stage control unit 38 and the lower control unit 37 may be arranged in one unit or may be arranged in the higher control unit 36.

The lower control unit 37 includes means for transmitting and receiving control signals to control the vacuum pump 4, the charged particle source 8, the optical lens 1, and the like. More specifically, in order to perform the three-dimensional internal structure observation, the lower control unit 37 includes means for controlling the vector parameter. That is, the lower control unit 37 can change and control the energy E and the irradiation angle θ of the charged particle beam that reaches the specimen from the charged particle beam source 8. In the drawing, an irradiation energy control unit 59 is illustrated between the lower control unit 37 and the charged particle optical lens tube 2. The irradiation energy control unit 59 is provided with a high-voltage power supply or the like that can define the energy E of irradiation of the specimen with the charged particle beam. The high-voltage power supply or the like that has the function of the irradiation energy control unit 59 may be inside the lower control unit 37. In addition, changing the energy E of irradiation of the specimen with the charged particle beam can be achieved either by changing the accelerating voltage generated from the charged particle beam source or by changing voltage supplied to the optical lens that can accelerate or decelerate the charged particle beam prior to the irradiation of the specimen with the charged particle beam. Alternatively, a power supply that can apply voltage to the specimen stage may be provided. Changing the irradiation angle θ can be realized by controlling an optical lens that enables irradiation with the charged particle beam to be tilted with respect to the optical axis 200. The lower control unit 37 also includes an A/D converter that converts an analog signal from the detector 3 or from the light detector 503 into a digital image signal and that transmits the digital image signal to the higher control unit 36. Data of the digital image signal is transmitted to the higher control unit 36. Analog circuits, digital circuits, and the like may be mixed in the lower control unit 37, or the higher control unit 36 and the lower control unit 37 may be unified.

Information about adjusting the position of the stage is transmitted to the stage control unit 38 by the higher control unit 36. The stage control unit 38 transmits drive information that is defined according to the information to the drive mechanisms 51 and 52. The specimen angle θ which is the vector parameter is also controlled in this manner.

A current control unit for controlling an optical lens that can change the beam current amount I of the charged particle beam is provided in the lower control unit 37. Alternatively, the high-voltage power supply as the irradiation energy control unit 59 may control the beam current amount I of the charged particle beam that is emitted from the electron source 8.

Next, the interior of the higher control unit 36 will be described. A data transmission and reception unit 40, a data memory unit 41, an external interface 42, and an operation unit 43 are included in the higher control unit. The data transmission and reception unit 40 receives data such as detected images and transmits data to the lower control unit 37 and to the stage control unit 38 so as to change the irradiation energy E and the irradiation angle θ. The data memory unit 41 stores digital detected signals transmitted from the lower control unit 37 as data. The external interface 42 transmits and receives signals with the user interface 34 such as a keyboard or a mouse used by the user of the device and with the monitor 35 on which the microscope image is displayed. The operation unit 43 performs operations on obtained data or on information of operations from the user. The detected image information may be read from the memory unit 41 and be displayed on the monitor 35 or may be stored as data on the memory. The detected image information may be displayed on the monitor 35 in a real-time manner. The higher control unit may be a computer such as a personal computer or a workstation or may be a controller substrate on which a CPU, a memory, and the like are mounted. In the higher control unit 36, after image data is stored on the memory unit 41 via the data transmission and reception unit 40, the operation unit 43 performs operations on the image data. The irradiation energy E and the irradiation angle θ which are the vector parameters can be controlled from the result of calculation via the data transmission and reception unit 40.

Figure 7:
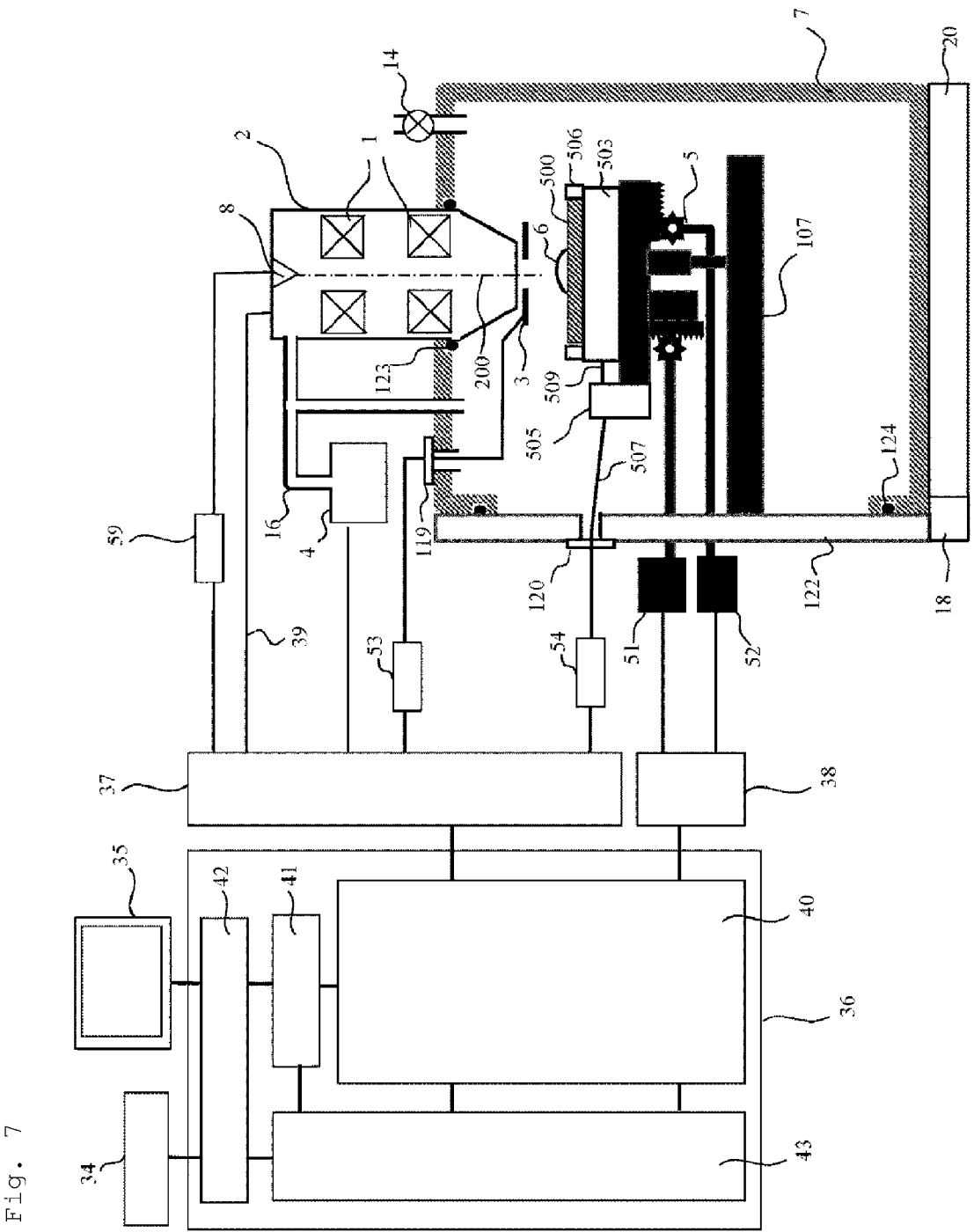
FIG. 7 is a descriptive diagram of a device in a first embodiment.

The configuration of the control system illustrated in FIG. 7 is merely an example. Modification examples of the control units, the valve, the vacuum pump, the communication interconnects, and the like fall in the scope of the charged particle beam microscope of the present embodiment as long as the functions intended in the present embodiment are satisfied.

The charged particle beam microscope, in addition, includes a control unit that controls operation of each part and an image generating unit that generates images on the basis of signals output from the detector (not illustrated). The control unit and the image generating unit may be configured as hardware by dedicated circuit substrates or may be configured as software that is executed by a computer connected to the charged particle beam microscope. The control unit and the image generating unit, in the case of being configured as hardware, can be realized by integrating a plurality of operators for performing processes on an interconnect substrate or in a semiconductor chip or package. The control unit and the image generating unit, in the case of being configured as software, can be realized by mounting a versatile high-speed CPU on a computer and by executing a program that performs a predetermined operation. A previously existing device may be upgraded by using a recording medium on which this program is recorded. The device, the circuits, and the computer are connected by a wired or wireless network in addition to the illustrated communication lines and transmit and receive data appropriately.

<Operating Screen>

Figure 8:
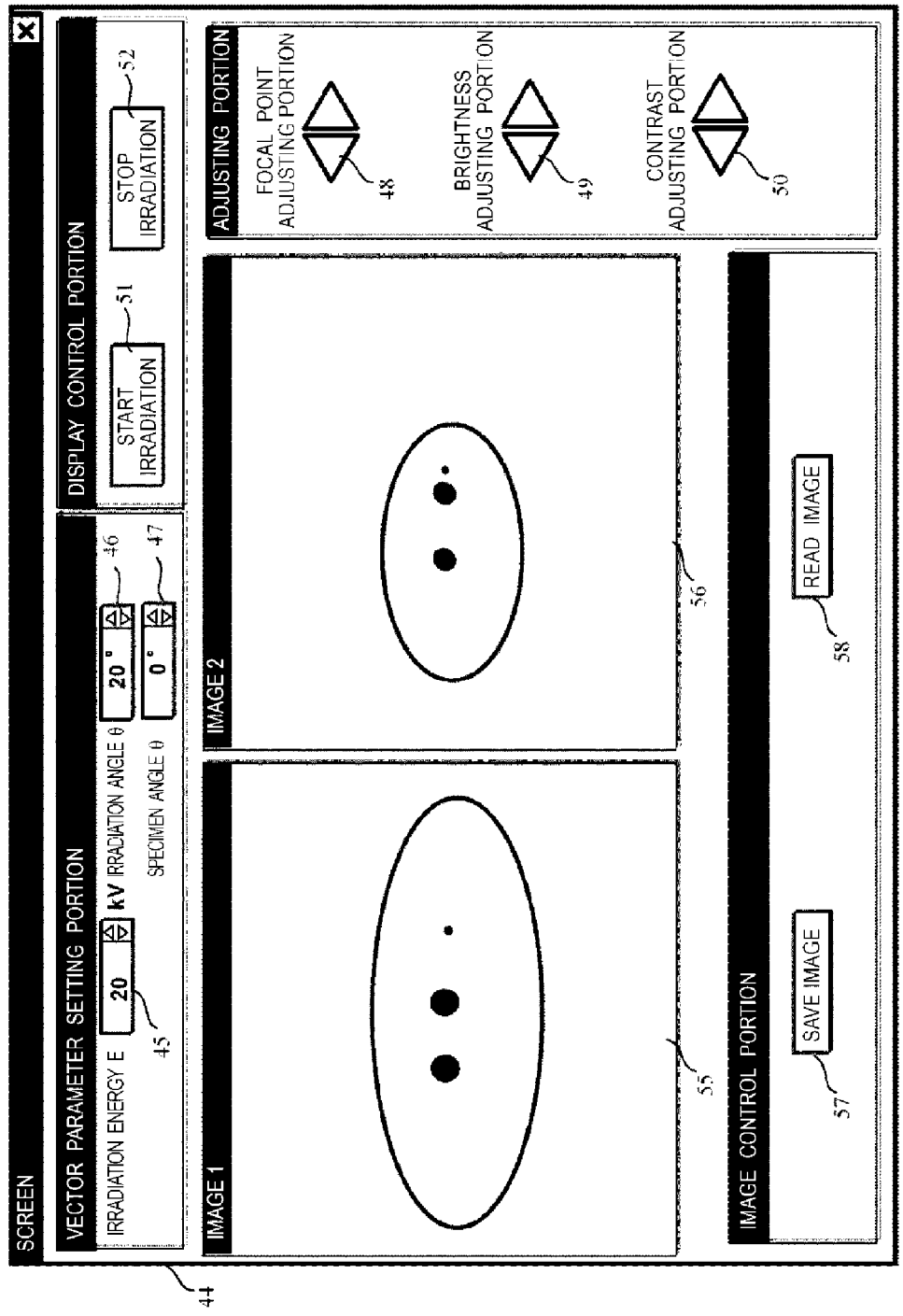
FIG. 8 is a descriptive diagram of an operating screen.

FIG. 8 illustrates an example of an operating screen. As a vector parameter setting unit that sets the vector parameter for observing the three-dimensional internal structure of the specimen, an irradiation energy E changing portion 45, an irradiation angle changing portion 46, and a specimen angle changing portion 47 are displayed on the monitor. The irradiation energy of the charged particle beam is set according to a numerical value that is input in the irradiation energy E changing portion 45. The irradiation angle changing portion 46 is an input window for changing the angle between the charged particle beam and the optical axis. The irradiation angle between the charged particle beam and the optical axis is set according to a numerical value input. The specimen angle changing portion 47 is an input window where an angle at which the specimen 6 is tilted is input. The specimen is tilted by tilting the specimen stage according to a numerical value input. Since the irradiation energy E which is the vector parameter corresponds to the density of an observable structure and the irradiation angle or the specimen angle corresponds to the direction of observation as described above, each input window on the operating screen may be displayed as an item such as "density" or "observation direction". It is also possible that only one of the irradiation angle changing portion 46 and the specimen angle changing portion 47 is provided. The operating screen is further configured of a focal point adjusting portion 48 where the focal point of the charged particle beam is changed, an image brightness adjusting portion 49, an image contrast adjusting portion 50, an irradiation start button 51, an irradiation stop button 52, and the like.

The operating screen is further provided with a screen 55 on which the microscope image can be displayed in a real-time manner, a screen 56 on which an image stored on the memory unit 41 can be displayed, and the like. The screen 56 on which an image stored on the memory unit 41 can be displayed may be displayed in a separate window or the like, and the screen 56 may be provided in quantities of two or more so that images obtained with different vector parameters are displayed on each screen. An image save button 57 for saving an image and an image read button 58 that enables reading an image are also displayed.

The user of the device can identify the three-dimensional internal structure of the specimen by obtaining a plurality of images displayed in a state where settings of the irradiation energy E and the irradiation angle θ which are the vector parameters are different and by displaying images of the transmitted charged particles that correspond to the plurality of vector parameters in a parallel manner. Instead of parallel display, or in addition to parallel display, display of these images may be switched for each arbitrary period of time. At this time, the user understands the three-dimensional structure more easily by displaying the images in order of magnitude of the vector parameters. The configuration of display illustrated in FIG. 8 is merely an example. Modification examples of the position of display, the form of display, and the like fall in the scope of the charged particle beam microscope of the present embodiment as long as the functions intended in the present embodiment are satisfied.

<Manual Observation Procedure>

Next, a procedure in which the user observes a three-dimensional internal structure will be described by using FIG. 9.

First, the user prepares the detecting element 500 (light-emitting specimen base) to mount the specimen. Next, a predetermined member is arranged on the detecting element 500 if necessary. The predetermined member is, as described above, a substance for increasing adhesion between the specimen and the specimen base, a conductive substance, a substance for reflecting light, any of predetermined gas materials, or the like. This step becomes unnecessary if arranging the predetermined member is not required. Next, the user mounts the specimen on the detecting element 500. Next, a transition is made to a step of mounting the detecting element 500 in either the charged particle microscope or the optical microscope to perform observation. A step A is a step of observation with the optical microscope, and a step B is a step of observation with the charged particle microscope.

In the step A of observation with the optical microscope, the user first arranges the detecting element 500 on which the specimen is mounted in the optical microscope device. As described above, if the shape of a slide glass is required when the detecting element 500 is arranged in the optical microscope device, the detecting element 500 may be mounted on a slide glass. Next, the user observes the specimen with the optical microscope. When the observation is finished, a transition is made to the step B of observation with the charged particle microscope device. If the optical microscope can obtain digital data as described below, the data may be moved to the higher control unit 36, and the optical microscope image may be displayed on the monitor 35.

In the step B, the user first arranges the detecting element 500 on which the specimen is mounted as described above in the charged particle microscope device. Next, in step 61, the irradiation energy E and the irradiation angle θ (or the beam current amount I) which are the vector parameters are set as desired on an operating screen 44 on the monitor 35.

Next, in step 62, the specimen is irradiated with the charged particle beam by the charged particle microscope, and light emitted from the specimen base 500 is detected. Next, in step 63, the image obtained in step 62 is displayed on the screen 55 on the monitor 35. Next, in step 64, the focal point of the optical lens is aligned to a desired position by adjusting the excitation intensity of the optical lens on the basis of user inputs on the operating screen. Next, in step 65, the brightness and contrast of the image at a desired position are adjusted by changing the ratio of amplification of a detected signal in the preamplifier substrate 505 on the basis of user inputs on the operating screen. When a desired image is obtained, next, the image data is stored on the memory unit 41 by saving the image in step 66. Next, in step 67, the user determines whether to change the vector parameters. If it is necessary to change the vector parameters, the process returns to step 61. If the vector parameters do not have to be changed, observation with the charged particle microscope device ends, and the specimen is withdrawn out of the charged particle microscope device. If necessary, the process returns to the step A of observation with the optical microscope. The steps A and B may be switched. In the case of a device into which the charged particle microscope device and the optical microscope device are integrated, the processes A and B may be alternately repeated, or observation may be performed at the same time. By performing this step, the three-dimensional internal structure of the specimen that is observed with the optical microscope can be observed with the charged particle beam microscope.

<Automatic Observation Procedure>

Figure 9:
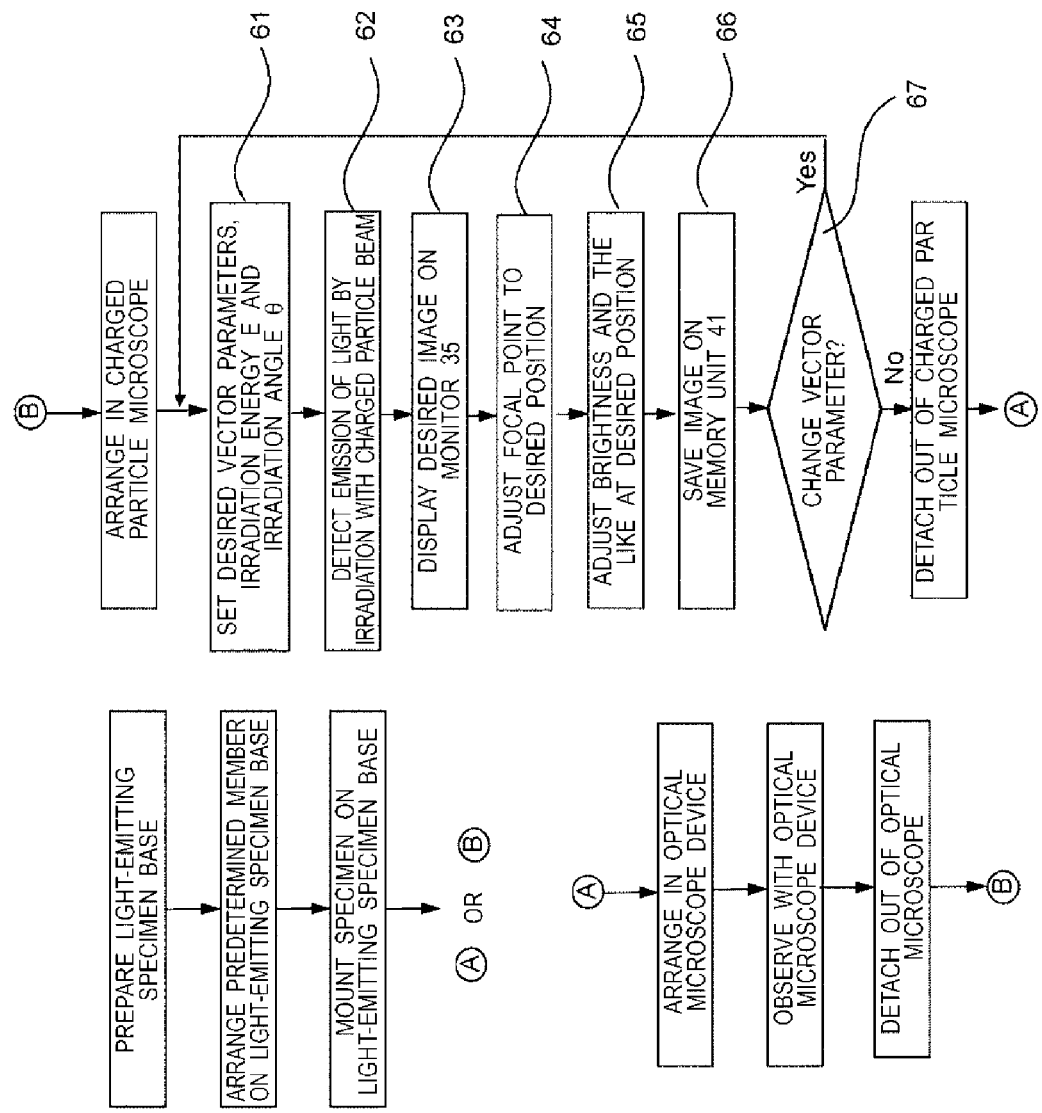
FIG. 9 is a descriptive diagram of a method for observation in the first embodiment.

Next, a configuration for automatically performing a procedure in which a series of operations and saving images for three-dimensional internal structure observation in the step B of FIG. 9 are performed will be described. Specifically, the procedure can be performed by automating step 61 to step 67.

Figure 10:
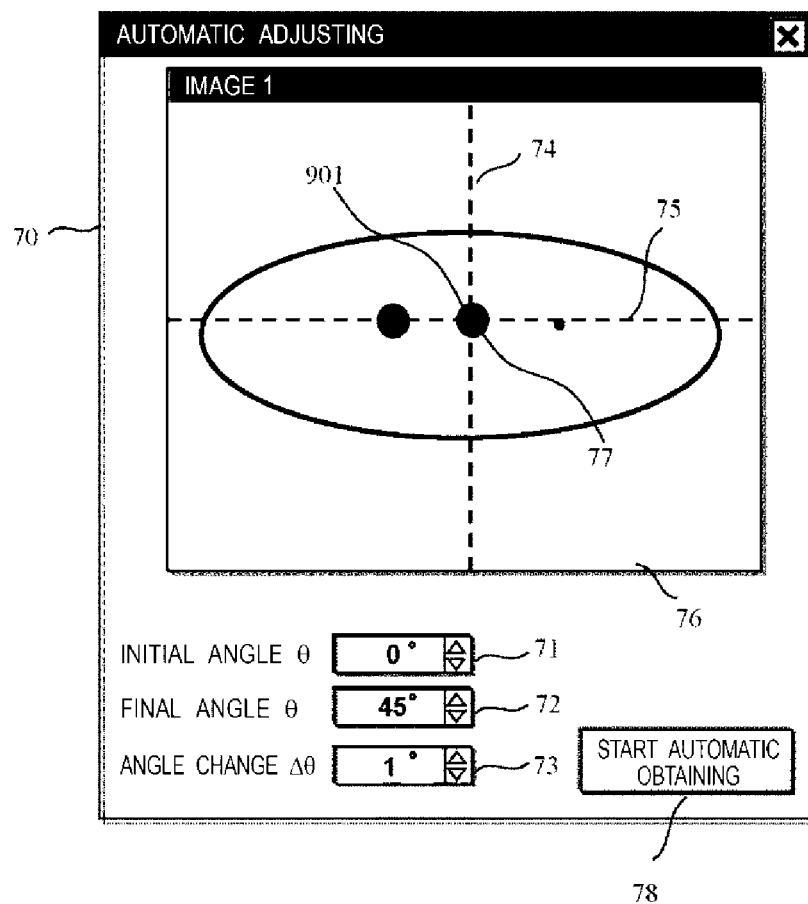
FIG. 10 is a descriptive diagram of an operating screen.

Hereinafter, a method for performing three-dimensional internal structure observation by changing the specimen angle θ will be described as an example by using an operating screen 70 illustrated in FIG. 10. The operating screen 70 is provided with an initial specimen angle θ setting portion 71, a final specimen angle θ setting portion 72, and an angle change Δθ setting portion 73 that defines a pitch width between the initial specimen angle and the final specimen angle. The specimen angle is changed by an angle Δθ that is set in the angle change Δθ setting portion 73 until the angle set in the initial specimen angle θ setting portion 71 becomes the angle set in the final specimen angle θ setting portion 72. The operating screen 70 is provided with a vertical setting bar 74, a horizontal setting bar 75, and a screen 76 on which the microscope image is displayed. The vertical setting bar 74 and the horizontal setting bar 75 are used to specify an object that defines a position which is always observed at the center of the image at the time of changing the angle θ. The point of intersection of the vertical setting bar 74 and the horizontal setting bar 75 is an automatic image obtaining reference point 77. The user adjusts the positions of the vertical setting bar 74 and the horizontal setting bar 75 such that the automatic image obtaining reference point 77 which the point of intersection between the vertical setting bar 74 and the horizontal setting bar 75 matches a position desired to be observed. A method for setting the automatic image obtaining reference point 77 is not limited to the above method as long as there is provided means for allowing the user to select a specific position on the specimen. The automatic image obtaining reference point 77 may not necessarily be the center of the screen. The drawing illustrates a state where the automatic image obtaining reference point 77 is set to match the internal substance 901. When the automatic image obtaining reference point 77 is set to the state in the drawing, the internal substance 901 can be always at the center of the image even if the angle θ of the specimen is changed. Furthermore, although the focal point and the brightness of the image also change if the angle θ of the slope is changed, the position, focal point, and brightness of the image are automatically adjusted with the part defined at the automatic image obtaining reference point 77 as a reference.

For example, the position of the internal substance 901 at the center of the screen moves to a position shifted from the left-right direction of the drawing if the specimen 6 is tilted. Thus, signals are transmitted to the drive mechanism 51 via the stage control unit 38 to automatically correct the position so that the part that is set as a reference point does not shift from the center of the screen before or after the angle θ of the slope which is the vector parameter is changed. The automatic image obtaining reference point may not necessarily be fixed to the center of the image. What is important is to correct the position of the stage such that the position on the specimen that is set as the automatic image obtaining reference point in the image of the transmitted charged particles does not change. These automatic adjustments are performed by the data transmission and reception unit 40, the data memory unit 41, and the operation unit 43 in the higher control unit 36 illustrated in FIG. 7. Particularly, automatic obtaining of the position is performed by the operation unit 43 that performs image calculation specifying where the structure at the automatic image obtaining reference point 77 is moved by the change of the angle θ of the slope. Afterward, by the operation unit 43, the focal point is automatically adjusted such that the focal point is aligned to the position of the automatic image obtaining reference point 77, and the brightness is adjusted such that the brightness of the position of the automatic image obtaining reference point 77 matches the brightness prior to tilting of the specimen. Accordingly, the focal point is always aligned, and the brightness becomes uniform before or after the change of the angle of the slope at the position on the specimen which is set as the automatic image obtaining reference point.

While only one automatic image obtaining reference point 77 is illustrated, the automatic image obtaining reference point 77 may be provided in plural quantities. The accuracy of automatic adjustments may be increased by pointing out the automatic image obtaining reference point 77 on the screen. After these settings are completed, it is possible to automatically perform step 61 to step 67 illustrated in FIG. 9 by pressing an automatic obtaining start button 78.

Images obtained during this period are stored on the data memory unit 41. The user of the device can identify the three-dimensional internal structure of the interior of the specimen by sequentially reading or lining up the continuously tilted images stored on the data memory unit 41 on the monitor. While only tilting of the specimen is described thus far, the same applies to the case of changing the irradiation energy E or the irradiation angle θ between the charged particle beam and the optical axis. In that case, the above description may be read by replacing "specimen angle θ" with "irradiation energy E", "irradiation angle θ between the charged particle beam and the optical axis", or "beam current amount I". Furthermore, images may be automatically obtained by changing the vector parameters of the irradiation energy E and the specimen angle θ at the same time.

The images that are manually or automatically obtained as described above may be converted into tomograms by a computed tomography (CT). If the images are converted into computed tomograms, the three-dimensional internal structure of the specimen can be displayed by freely rotating the images on the monitor, and furthermore, it is possible to display only a specific cross section. If representing a specimen such as a cell promptly as a computed tomogram is desired, the specimen may be moved automatically. In this case, the irradiation angle θ, the energy E of the charged particle beam, and the beam current amount I of the charged particle beam may be changed as a set in a real-time manner.

Although illustration is not provided, stereo observation may be performed by tilting the above two saved or displayed images by a few degrees for stereoscopic observation. In the case of stereoscopic observation, two images that are captured by changing angles may be lined up and viewed stereoscopically. Alternatively, an image on which images where two types of colors such as blue and red are changed are superimposed may be used. Alternatively, the images may be three-dimensionally displayed on a display unit such as a monitor that allows three-dimensional observation.

<Immunostaining>

Immunostaining that attaches labels such as colloidal gold may be performed on the specimen. By labeling the specimen, it is possible to observe not only the structure of the interior of the specimen but also a location where a protein or the like desired to be detected exists locally in the specimen. A case of observing the labeled specimen is considered in FIG. 11. The specimen in this case is, for example, a cultured cell or a cell removed from a living body. If a material to which an antibody joined to a gold label 909 is added is injected into the cell, the material reacts specifically with a protein or the like in the cell and is joined thereto (antigen-antibody reaction). The charged particle beam 900 is mostly scattered by the gold label 909. Thus, a projected image (or a detected image) 910 looks like the drawing, and a location where the gold label 909 exists locally is obtained. As a consequence, a location of a protein or the like desired to be detected can be obtained.

It is also possible to obtain a location where a protein or the like desired to be detected is concentrated by performing three-dimensional internal structure observation, CT observation, or the like by changing the vector parameters (changing the specimen angle θ in the drawing) as illustrated in FIG. 11(a) to FIG. 11(b). The gold label 909 may have a variety of sizes from a few nm to a few μm. The amount of the charged particle beam 900 scattered differs depending on the density of or amount of the gold label 909 concentrated. That is, for example, by adjusting the irradiation energy E, it is possible to detect a light-colored gold label portion 911 (alternatively, an unillustrated deep-colored gold label portion) or the like in the projected image 910. Since the position, density, and the like of a protein that is specifically concentrated are represented in the projected image 910, the user can obtain the position and density of a protein in the cell by looking at the image. The size, depth of color, and the like of the gold label portion may be set only enough for observation of the user of the device, or the size and the depth of color may be measured and determined in the higher control unit 36.

The elements or chemical state of the interior of the specimen may be analyzed by, although illustration is not provided, obtaining radiations such as X-rays generated by irradiation with the charged particle beam.

<Description of Microscope Information Exchange>

Figure 12:
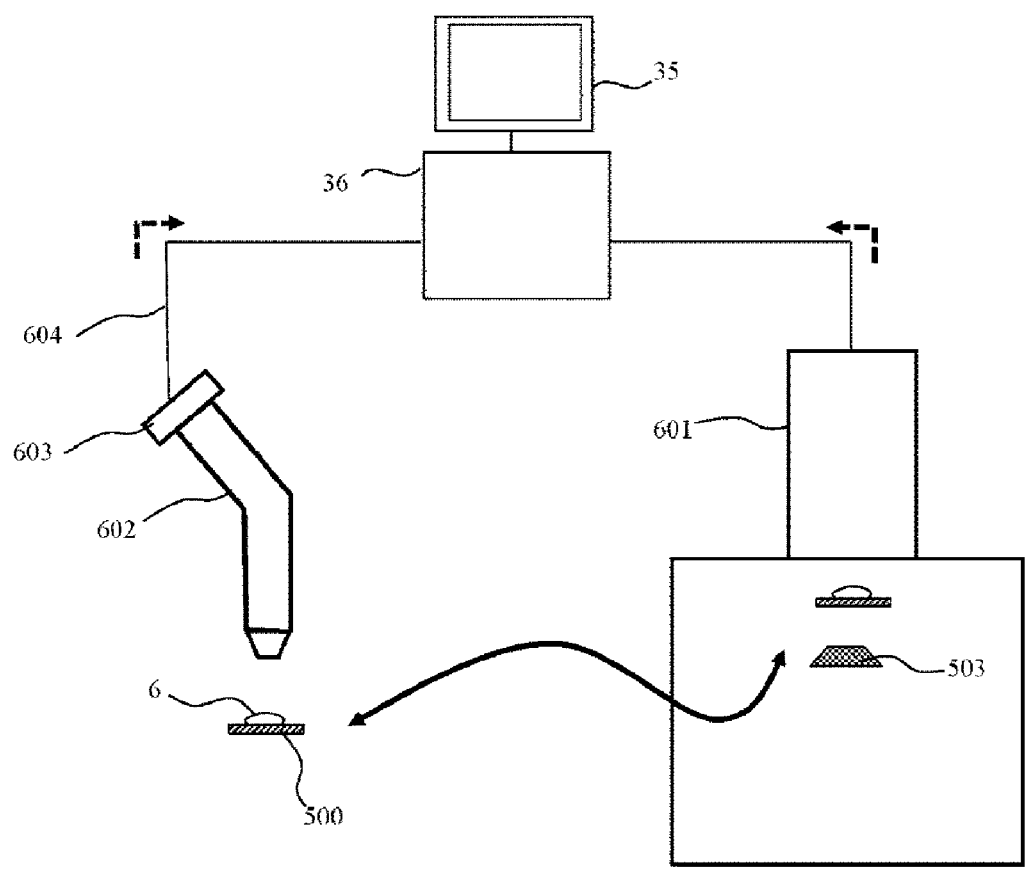
FIG. 12 is a schematic descriptive diagram of optical microscopic observation and charged particle beam microscopic observation.

As described above, the specimen can be observed with the optical microscope and with the charged particle microscope on the same specimen base by mounting the specimen desired to be observed on the specimen base. At this time, observing the same part accurately with the optical microscope and with the charged particle microscope is desired. Therefore, a device system that can observe the same part with the optical microscope and with the charged particle microscope will be described by using FIG. 12. An optical microscope 602 is provided with a CCD camera 603. The user first obtains an image of the specimen with the optical microscope. The CCD camera 603 and the higher control unit 36 are connected by an interconnect 604. Accordingly, digital image information of the optical microscope can be transmitted to the higher control unit 36 as illustrated by a dotted line arrow in the drawing. In addition, image information obtained in the charged particle microscope is also transmitted to the higher control unit 36 in the same manner. Thus, microscope images of the same part can be compared on the same monitor 35. The user searches for the position on the specimen for obtaining an image with the charged particle microscope while looking at the image obtained by the optical microscope on the monitor. Accordingly, a desired position on the specimen can be arranged at the position where irradiation is performed with the primary charged particle beam on the basis of the result of observation with the optical microscope. The user may search for a position on the specimen that has a shape similar to the optical microscope image through operation processes such as image matching and similarity calculation and may automatically set the position as the position where irradiation is performed with the charged particle beam. Although illustration is not provided, a separate computer may be interposed between the optical microscope and the higher control unit, or image information may be transmitted therebetween via a communication line such as the Internet.

Figure 13:
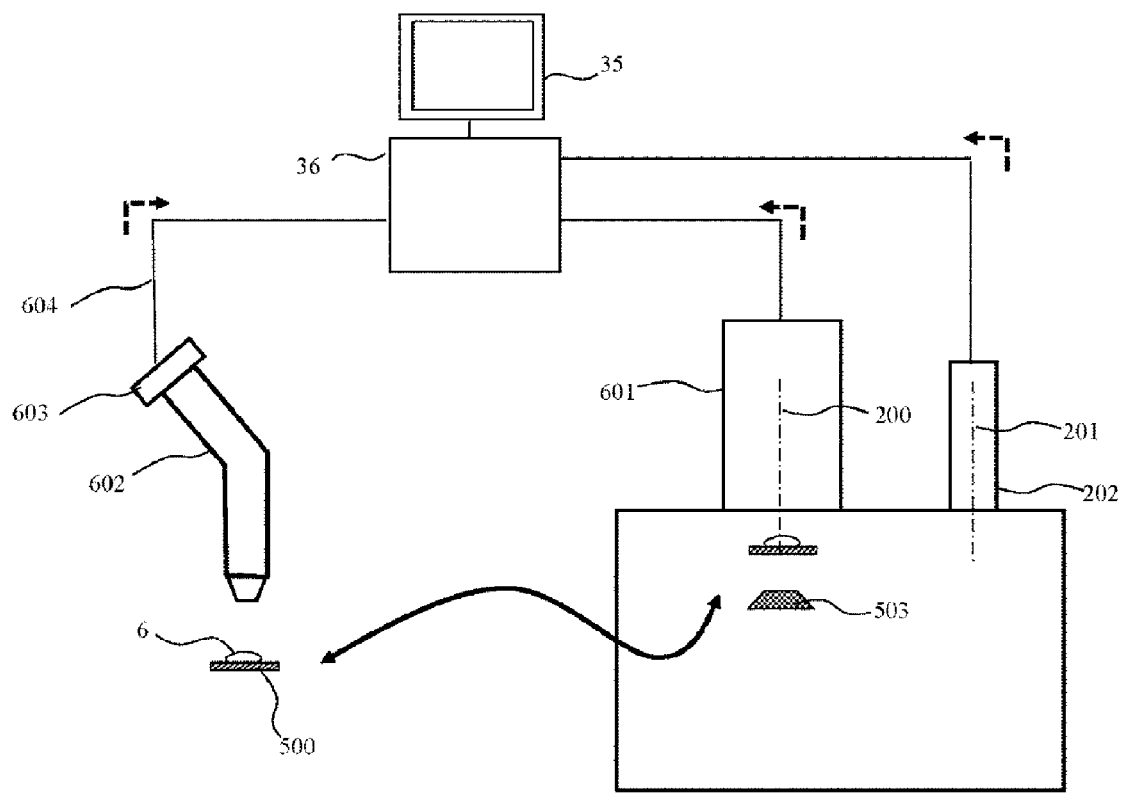
FIG. 13 is a schematic descriptive diagram of optical microscopic observation and charged particle beam microscopic observation.

A simple optical microscope 202 may be arranged in the charged particle microscope device 601 as illustrated in FIG. 13. The word "simple" means that optical microscopic observation can be simply performed with, for example, a fixed magnification, a small size, or an inexpensive price. The optical microscope 202 includes a simple image formation system such as an optical lens and a capturing element such as a CCD camera. Image information from the optical microscope 202 is connected to the higher control unit 36 in the same manner via an interconnect. The distance between the optical axis 200 of the charged particle microscope and an optical axis 201 of the optical microscope 202 is always constant. Thus, the distance by which a location is moved after observation with the optical microscope is also constant at all times. Therefore, if there is provided a configuration in which this distance is stored in advance on a memory or the like and in which the drive units 51 and 52 are controlled with this distance value as the amount of movement of the stage at the time of input of a stage moving instruction, the user can provide the instruction for movement between the optical axis 200 of the charged particle microscope and the optical axis 201 of the optical microscope 202 with a very simple operation. Therefore, observing the same part of the specimen with the simple optical microscope 202 and with the charged particle microscope 601 is greatly facilitated.

Both the optical microscope 602 and the optical microscope 202 use light, and thus images obtained look almost the same. Therefore, observing the same part of the specimen that is observed with the optical microscope 602 is greatly facilitated with the charged particle microscope 601. Specifically, observation is performed in the following procedure. The user first observes a desired position on the specimen with the optical microscope 602 that is installed outside the charged particle microscope device and then introduces the specimen base on which the specimen is mounted into the charged particle microscope device. Next, the user specifies the position observed with the optical microscope 602 by using the optical microscope 202. This work may be performed manually by the user or may be performed automatically by performing operation processes such as matching and similarity calculation based on the image obtained with the optical microscope 602. Next, the specimen is moved from the optical microscope 202 to the charged particle microscope 601 in the above method, and the position on the specimen specified by the optical microscope 202 is arranged at the position where irradiation is performed with the primary charged particle beam. Next, an image of the transmitted charged particles is obtained by the charged particle microscope. As such, by using the optical microscope 202 for aligning positions of observation between the optical microscope outside the charged particle beam microscope device and the charged particle microscope, observing the position on the specimen that is observed with the optical microscope outside the charged particle microscope device is greatly simplified with the charged particle microscope.

Figure 14:
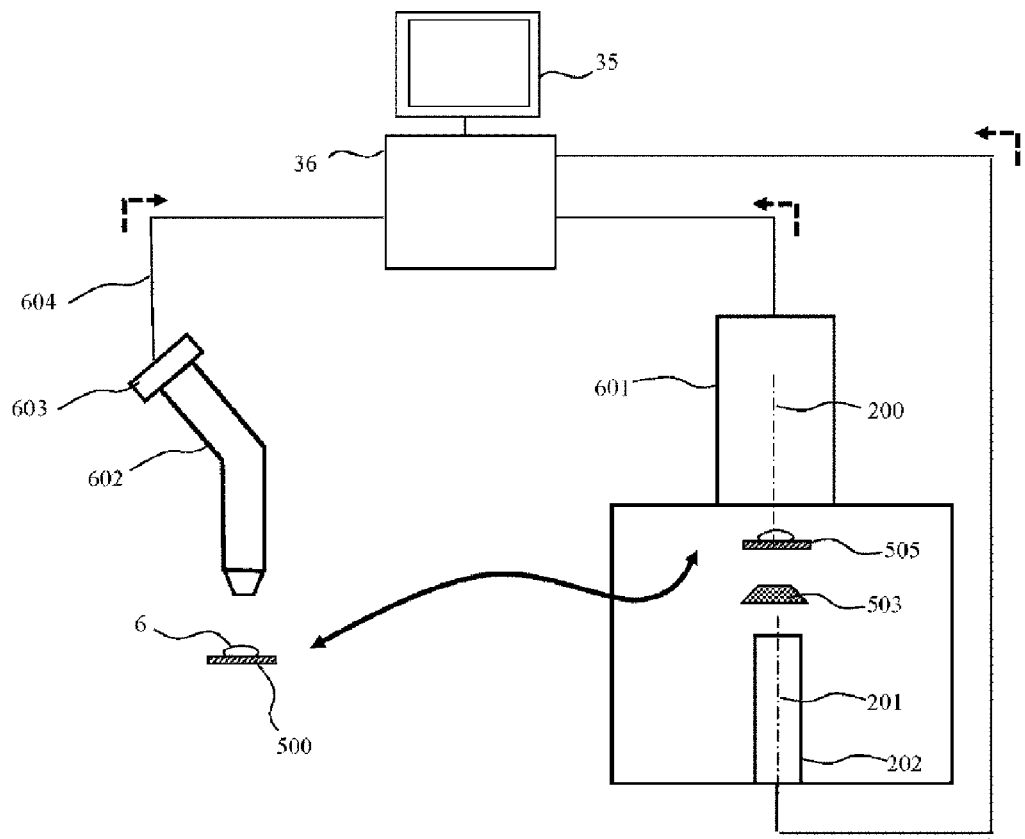
FIG. 14 is a schematic descriptive diagram of optical microscopic observation and charged particle beam microscopic observation.

The optical axis 200 of the charged particle microscope and the optical axis 201 of the optical microscope 202 may be set as the same axis by allowing the location of the optical microscope 202 to be arranged directly under the specimen base 500 as illustrated in FIG. 14. The optical axis 200 of the charged particle microscope and the optical axis 201 of the optical microscope 202 being the same axis allows observation of the same part, and both the optical microscope 602 and the optical microscope 202 use light. Thus, observing the same part of the specimen is greatly simplified. As a consequence, the same part of the specimen that is observed with the optical microscope 602 can be observed with the charged particle microscope 601 more easily than the configuration of FIG. 13. In the case of observation with the optical microscope 202, the light detector 503 may be detached or may be configured to change the position thereof by providing a moving mechanism in the light detector 503. The transmission charged particle microscope image may be formed by obtaining light from the detecting element 500 via the optical microscope 202.

The optical microscope 202 can also be used in the case of FIG. 14 for aligning positions of observation between the optical microscope outside the charged particle beam microscope device and the charged particle microscope in the same manner as described in FIG. 13. In this case, it is not necessary to perform a step of moving the specimen from the optical microscope 202 to the charged particle microscope 601.

Figure 15:
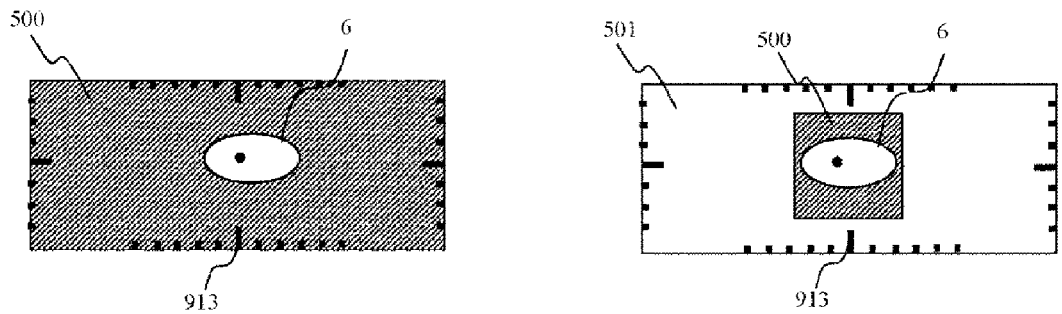
FIG. 15 is a detailed diagram of the specimen base that is provided with the detecting element.

It may be difficult to immediately find the location observed with the optical microscope in the charged particle beam microscope. Therefore, hereinafter, means for sharing positional information between the optical microscope and the charged particle microscope will be described next. What is considered as the means for sharing positional information between the microscopes is a method of simply finding a location desired to be observed by using a mark on the specimen base. FIG. 15 illustrates a top view of the detecting element 500 on which the specimen 6 is mounted. The detecting element 500 that is the specimen base is provided with a marking 913 that enables obtaining of the positional relationship of the specimen with respect to the detecting element 500. The marking 913 is formed at a predetermined position on the specimen base and is a mark that has a known pitch width such as a ruler. Since the marking is formed horizontally and vertically, it is possible to find which location is observed. If the detecting element 500 is arranged on the base 501 that is provided with a marking when it is difficult to form a marking on the detecting element 500, it is possible to find where the specimen is arranged on the specimen base. The position of observation may be obtained by recording a plurality of points as marks somewhere on the specimen base and by using the points as reference points. For example, the specimen may be used as a reference point. The user of the device may perform a work of storing the position of the specimen on the basis of the marking, or the work may be performed on the higher control unit 36 or the like by creating map data of the specimen base and by searching for the position on the basis of the map data stored on a memory.

As described thus far, the three-dimensional internal structure of the specimen that is observed with the optical microscope can be observed with the charged particle microscope by using the charged particle beam device, the specimen observation method, the specimen base, and the observation system of the present embodiment.

Second Embodiment

The specimen base configured as a light-emitting element is described in the first embodiment. In the present embodiment, a case where the specimen base is a semiconductor detecting element that can generate electrons and positive holes when being irradiated with the charged particle beam will be described. Hereinafter, the same part as the first embodiment will not be described.

Figure 16:
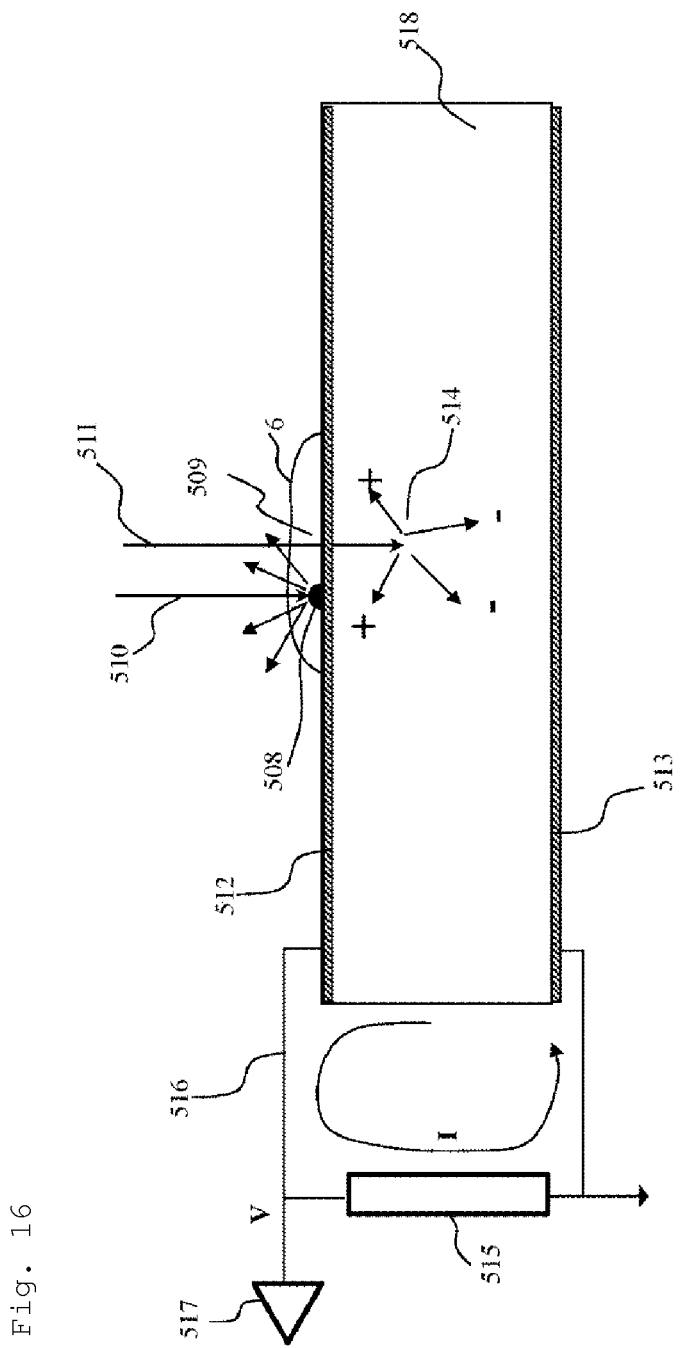
FIG. 16 is a descriptive diagram of a detecting element in a second embodiment.

A principle and configuration will be described by using FIG. 16. The specimen 6 is provided on a specimen base 518 that can generate electrons and positive holes when being irradiated with the charged particle beam. The specimen base 501 is a semiconductor detecting element or the like, and there exist a P layer, an N layer, a depletion layer, and the like inside the specimen base 501. Even in this case, the specimen base 518 detects charged particles that are transmitted through or scattered by the interior of the specimen in the same manner as the first embodiment. The detecting element that doubles as the specimen base is provided with thin layers such as an upper layer portion 512 and a lower layer portion 513. These thin layers are made of a material that allows flow of electricity and is, for example, metal films. Although the thin films are illustrated on the entire surfaces of the detecting element in the drawing, the thin films may be provided at a part thereof.

A case where there are the high-density part 508 and the low-density part 509 in the specimen is considered. When the high-density part 508 of the specimen is irradiated with the primary charged particle beam 510, the charged particle beam is mostly backscattered. Thus, the charged particle beam does not reach the detecting element 518. Meanwhile, when the low-density part 509 of the specimen is irradiated with a primary charged particle beam 511, the charged particle beam can be transmitted to the detecting element 518. The charged particle beam that reaches the detecting element 518 generates a pair of electron positive holes 514 in the detecting element 518. By the generation of the pair of electron positive holes 514, positive holes or electrons are attracted to the upper layer portion 512 and to the lower layer portion 513. If a resistor 515 that is outside the detecting element which doubles as the specimen base is connected between the upper layer portion 512 and the lower layer portion 513 through an interconnect 516 or the like, the pair of electron positive holes enables a current I to flow and, in turn, generates a voltage V across the resistor 515. By amplifying the voltage V with an amplifier 517, signals can be amplified. As a consequence of a series of these actions, a density difference in the specimen can be detected by obtaining signals from the detecting element 518.

The inelastic mean free path of a charged particle beam depends on the accelerating voltage of the charged particle beam and ranges from a few tens of nm to a few tens of Thus, the thickness of the upper layer portion 512 is required to be approximately the same on the upper face of the detecting element 518. While the specimen 6 is in contact with the upper layer portion 512 in the drawing, the specimen may not be mounted on the upper layer portion 512 in terms of toxicity or the like of the upper layer portion 512 when the specimen is a biological specimen or the like. Therefore, a material that has high affinity with biological specimens such as collagen may be applied onto the specimen. The material may be arranged between the upper layer portion 512 and the specimen 6.

As described in the first embodiment, if the specimen 6 is a hydrated material or the like, the thin film 702 may be arranged around the specimen, or water in the specimen may be replaced by the replacement substance 703 such as ionic liquid.

Figure 17:
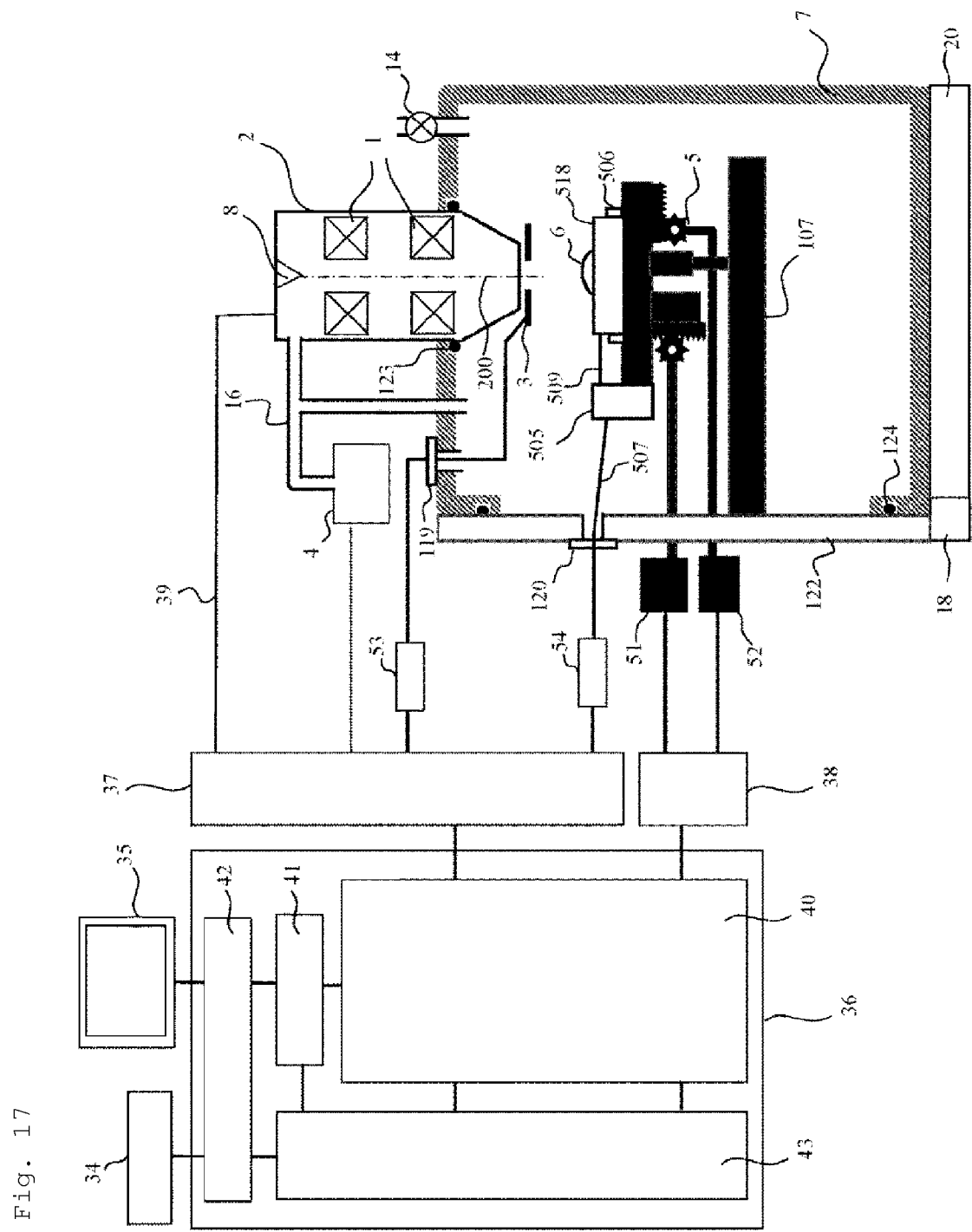
FIG. 17 is a descriptive diagram of a device in the second embodiment.

FIG. 17 illustrates a configuration of a device for performing three-dimensional internal structure observation by using the semiconductor detecting element of the present embodiment. In FIG. 17, the semiconductor detecting element 518 that is the specimen base is arranged on the specimen stage 5. The preamplifier substrate 505 is connected via the interconnect 509 to the detecting element 518 provided in the stage 5. The preamplifier substrate 505 is connected to the lower control unit 37 via the interconnect 507 or the like. While the preamplifier substrate 505 is inside the casing 7 in the drawing, the preamplifier substrate 505 may be outside the casing 7 (for example, at the preamplifier 54 part in the drawing). It is necessary to prevent the specimen base 518 from falling from the specimen stage 5 at the time of tilting the specimen base 518. Thus, the fixing member 506 that can define a position to arrange the specimen base 518 on the specimen stage 5 is provided. In addition, an unillustrated fixing member may be provided between the specimen base 518 and the specimen stage 5. Accordingly, it is possible to fix the specimen base 518 and to prevent positional shifting. When the specimen base is introduced into or detached from the device, the specimen base 518 is attached to or detached from the specimen stage 5 by connecting or detaching the interconnect 509 to or from the specimen stage 5.

Third Embodiment

The word "atmospheric pressure" in the following embodiment means an atmospheric or slightly negative pressure environment in the atmosphere or in a predetermined gas atmosphere. Specifically, the atmospheric pressure ranges from approximately $10^5$ Pa (atmospheric pressure) to $10^3$ Pa.

<Description of Observation with Charged Particle Beam Device Under Atmospheric Pressure>

Next, an example in which a charged particle beam device that enables observation under atmospheric pressure is used will be described by using FIG. 18. A basic configuration of the charged particle microscope is the same as that of FIG. 7. Thus, only features of the device for observation under atmospheric pressure will be mainly described in the present embodiment.

Figure 18:
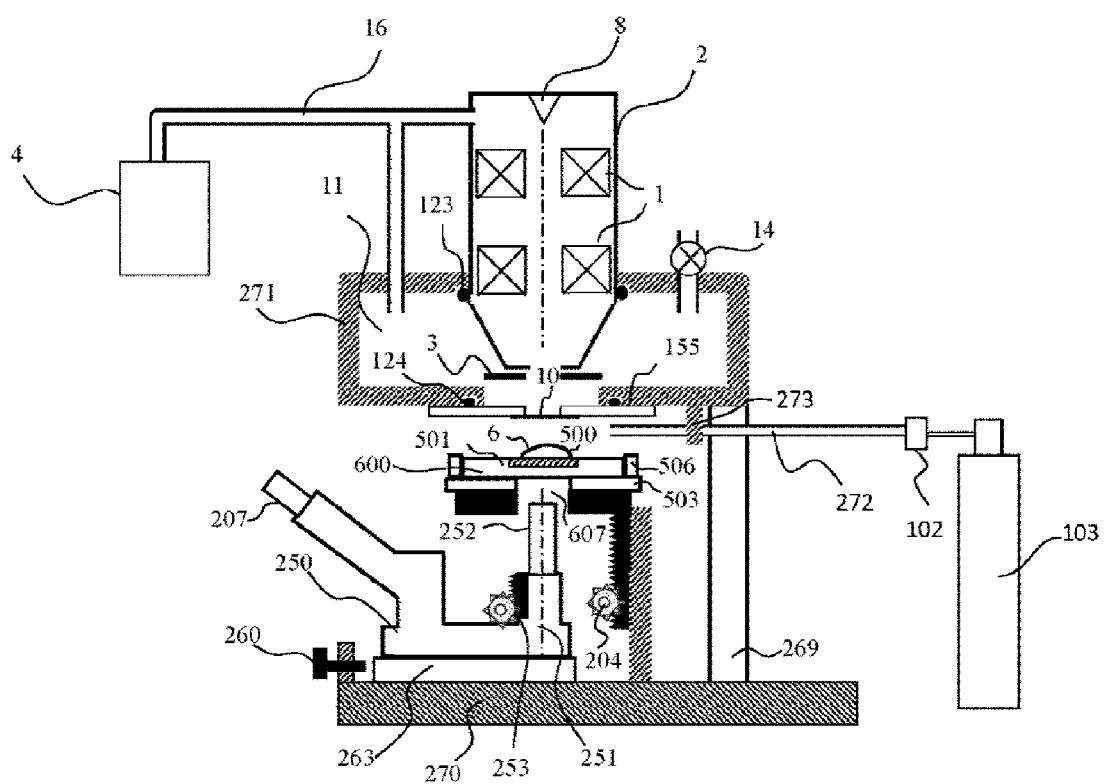
FIG. 18 is a descriptive diagram of a device in a third embodiment.

FIG. 18 illustrates the entire configuration of the charged particle microscope of the present embodiment. In the present embodiment, the charged particle optical lens tube 2 is embedded in a casing 271 and is sealed in a vacuum by the vacuum seal member 123. The casing 271 is supported by a post 269. The post 269 is supported by a base 270. While only one post 269 is illustrated in the drawing, the post 269 is preferably provided in plural quantities in actuality to support the casing. According to this configuration, the atmosphere of the specimen 6 becomes equal to that outside the device. Thus the specimen can be exposed to a complete atmospheric state.

A partition film 10 through which the charged particle beam can be transmitted or pass is disposed between the charged particle optical lens tube and the specimen. The partition film 10 is attachable to and detachable from the casing 271. The vacuum pump 4 is connected to the casing 271 so that the air in a closed space configured of the inner wall faces of the casing 271 and the partition film 10 (hereinafter, referred to as a first space) can be exhausted to make a vacuum therein. Accordingly, in the present embodiment, while a high vacuum is maintained in a first space 11 by the partition film 10, a gas atmosphere under atmospheric pressure or under pressure that is approximately the same as atmospheric pressure is maintained in a space where the specimen is mounted. Therefore, a vacuum state can be maintained on the charged particle optical lens tube 2 side during operation of the device, and an atmospheric pressure or predetermined pressure atmosphere can be maintained around the specimen 6 and the specimen base. The partition film 10 is retained by a partition film retaining member 155. Exchanging the partition film 10 is available by exchanging the partition film retaining member 155.

A gas nozzle 272 supplies gas from a gas cylinder 103 toward the vicinity of the specimen 6. The gas nozzle 272, for example, is connected to the casing 271 by a support 273. The gas cylinder 103 and the gas nozzle 272 are connected by a connecting portion 102. While the configuration is merely an example, the present configuration enables a desired gas to be ejected to the vicinity of the specimen 6. Types of gases include nitrogen that is lighter than the atmosphere, a vapor, a helium gas, a hydrogen gas, and the like so as to reduce scattering of the electron beam. The user can exchange the gas freely. The gas cylinder 103 may be replaced with a vacuum pump so that a vacuum can be made between the partition film 10 and the specimen 6.

An optical microscope 250 is arranged directly under the casing 271, that is, at the same axis as the optical axis of the charged particle optical lens tube. Accordingly, it is possible to obtain a charged particle beam microscope image by irradiating the specimen 6 on the specimen base arranged on the specimen stage 5 with the charged particle beam that passes through the partition film 10 and to obtain the optical microscope image by the optical microscope 250. However, the arrangement of the optical microscope is not limited to this as described in the above embodiment.

The specimen base that is provided with the detecting element 500 can be mounted on the specimen stage 5 of the charged particle beam device. While the specimen base is mounted on the specimen stage, the detecting element 500 is mounted on the opposite side of the specimen from the partition film. The configuration of arrangement of the light detector 503 and the like near the specimen stage is the same as those in the first and second embodiments. In the case of the present configuration, transmitted charged particle beam signals can be obtained by reducing a shape change such as evaporation of water that occurs because of making a vacuum or the like as much as possible. In addition, since it is not necessary to make a high vacuum in the space around the specimen, transmission charged particle beam microscope images of the specimen can be obtained with very high throughput. In addition, since the space where the specimen is arranged is not limited in the configuration of the present embodiment, this configuration is useful in a case where the size of the specimen base is very large.

Fourth Embodiment

Figure 19:
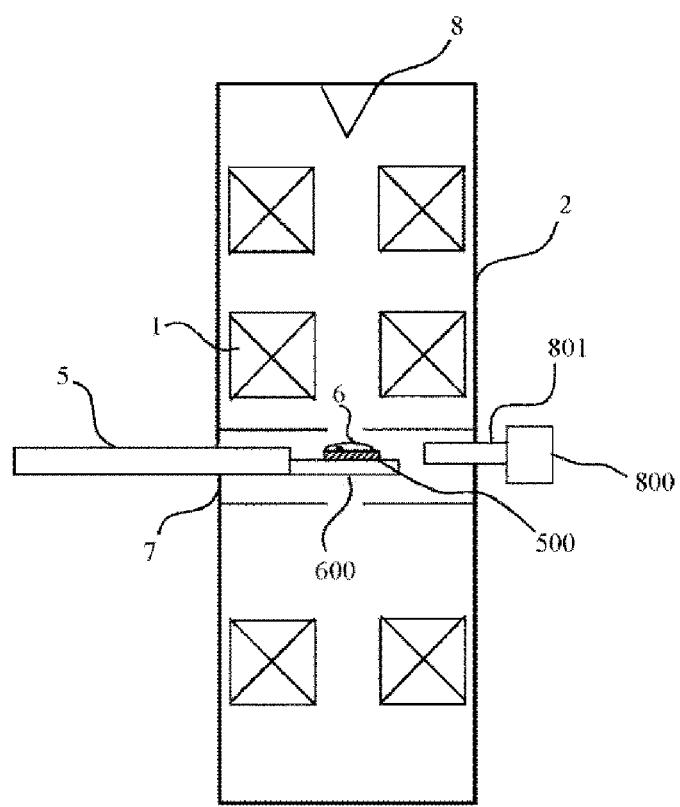
FIG. 19 is a descriptive diagram of a device in a fourth embodiment.

Next, a configuration of a side entry device into which the specimen and the specimen base are introduced from a small region on a side face of the casing 7 will be described by using FIG. 19. Hereinafter, the same part as the first to third embodiments will not be described.

The specimen stage 5 is introduced into the device such that the specimen stage 5 is inserted from a narrow region that is a part of the casing 7. A control system for controlling each optical lens, a detection system for detecting detected signals, a vacuum pump for exhausting the air inside the casing 7 or inside the charged particle optical lens tube 2, and the like, since self-evident, will not be described. Emission of light from the detecting element 500 on which the specimen 6 is mounted either directly or indirectly is detected by a light detector 800 that is arranged in the casing 7 or the like through a light transmission path 801. The light detector for detecting emission of light from the detecting element 500 is favorably arranged inside or outside the casing 7 or at anywhere of a specimen base 500, the specimen stage 5, or the optical lens tube 2 in the drawing. The position or modification examples of the light amplifier and the light transmission path fall in the scope of the charged particle beam microscope of the present embodiment as long as the functions intended in the present embodiment are satisfied. In the present configuration, for example, a mechanism that can change the specimen angle θ which is the vector parameter is provided in the specimen stage 5. In the case of the present configuration, the size of the specimen stage 5 can be smaller than that of the above embodiments. Thus, the tilting mechanism on the specimen stage 5 can be significantly simplified.

The present invention is not limited to the above embodiments and includes various modification examples. For example, the above embodiments are described in detail in order to facilitate understanding of the present invention. The present invention is not limited to the embodiments that include all of the described configurations. In addition, it is possible to replace apart of configurations of an embodiment with configurations of another embodiment. It is also possible to add configurations of an embodiment to configurations of another embodiment. In addition, a part of the configuration of each embodiment may be removed or replaced with another configuration, or another configuration may be added thereto. A part or the entirety of each of the above configurations, functions, processing units, processing means, and the like may be realized by hardware, such as by designing integrated circuits therefor. Each of the above configurations, functions, and the like may be realized by software by a processor that interprets and executes programs which realize each function. Information such as programs, tables, and files realizing each function can reside on a recording device such as a memory, a hard disk, or a solid-state drive (SSD) or on a recording medium such as an IC card, an SD card, or an optical disc.

Illustrations are provided of only control lines and information lines that are considered as necessary for description, and not all control lines and information lines of a product are necessarily illustrated. In actuality, almost all of the configurations may be considered as being connected to each other.

REFERENCE SIGNS LIST 1 optical lens
2 charged particle optical lens tube
3 detector
4 vacuum pump
5 specimen stage
6 specimen
7 casing
8 charged particle source
10 partition film
11 first space
14 leak valve
16 vacuum pipe
18 supportive post
19 lid member supporting member
20 bottom plate
34 user interface such as keyboard or mouse
35 monitor
36 higher control unit
37 lower control unit
38 stage control unit
39 communication line
40 data transmission and reception unit
41 data memory unit
42 external interface
43 operation unit
44 operating screen
45 irradiation energy changing portion
46 irradiation angle changing portion
47 specimen angle changing portion
48 focal point adjusting portion
49 brightness adjusting portion
50 contrast adjusting portion
51 irradiation start button
52 irradiation stop button
53 preamplifier
54 preamplifier
55 screen
56 screen
57 image save button
58 image read button
59 irradiation energy control unit
61, 62, 63, 64, 65, 66, 67 step
70 operating screen
71 initial specimen angle θ setting portion
72 final specimen angle θ setting portion
73 angle change Δθ setting portion
74 vertical setting bar
75 horizontal setting bar
76 screen
77 automatic image obtaining reference point
78 automatic obtaining start button
102 connecting portion
103 gas cylinder
107 supportive plate
119 hermetic seal
120 hermetic seal
122 lid member
123, 124, 125, 126, 128, 129 vacuum seal member
155 partition film retaining member
200 optical axis of charged particle microscope
201 optical axis of optical microscope
202 optical microscope
250 optical microscope
269 post
270 base
271 casing
272 gas nozzle
500 specimen base or detecting element
501 base
502 thin film
503 light detector
505 preamplifier substrate
506 fixing member
507 interconnect
508 high-density part
509 low-density part
510 primary charged particle beam
511 primary charged particle beam
512 upper layer portion
513 lower layer portion
514 pair of electron positive holes
515 resistor
516 interconnect
517 amplifier
518 detecting element
601 charged particle beam microscope
602 optical microscope
603 CCD camera
604 interconnect
702 thin film
703 replacement substance
800 light detector
801 light transmission path
900 charged particle beam
901 internal structure
902 internal structure
903 internal structure
903a projected internal structure
903, 904 substance
905 optical axis
906 projected image (or detected image)
907 projected image (or detected image)
908 projected image (or detected image)
909 gold label
910 projected image (or detected image)
911 gold label
912 projected image (or detected image)
913 marking

The invention claimed is:

1. A charged particle beam device comprising:
a charged particle optical lens tube that irradiates a specimen with a primary charged particle beam;
a specimen stage in which a specimen base that retains the specimen is arranged in an attachable and detachable manner; and
a control unit that controls a vector parameter which defines the interrelationship between the primary charged particle beam and the specimen,
wherein the specimen base is configured to include a detector that detects charged particles which are transmitted through or scattered by the interior of the specimen, and by irradiation with the primary charged particle beam with a plurality of different vector parameters, images of transmitted charged particles of the specimen that correspond to each of the vector parameters are obtained.

2. The charged particle beam device according to claim 1, further comprising:
a specimen stage drive mechanism that is capable of tilting the specimen with respect to the optical axis of the primary charged particle beam,
wherein the vector parameter includes the relative angle between the direction of incidence of the primary charged particle beam and the specimen.

3. The charged particle beam device according to claim 1, further comprising:
at least one of a charged particle beam source that changes the incident energy of the primary charged particle beam, an optical lens to which voltage that accelerates or decelerates the primary charged particle beam is applied, and a power supply that applies voltage to the specimen stage,
wherein the vector parameter includes the incident energy of the primary charged particle beam.

4. The charged particle beam device according to claim 1, further comprising:
an optical lens that causes the primary charged particle beam to be incident on the specimen slantwise with respect to the optical axis of the primary charged particle beam,
wherein the vector parameter includes the relative angle between the direction of incidence of the primary charged particle beam and the specimen.

5. The charged particle beam device according to claim 1, further comprising:
an optical lens or a current control unit, either of which is capable of changing the amount of an irradiation current of the primary charged particle beam,
wherein the vector parameter includes the amount of a current of the primary charged particle beam that is incident on the specimen.

6. The charged particle beam device according to claim 1, further comprising:
a monitor that displays a plurality of images of transmitted charged particles corresponding to each of the vector parameters in a parallel manner.

7. The charged particle beam device according to claim 1, further comprising:
a monitor that displays a plurality of images of transmitted charged particles corresponding to each of the vector parameters in order of magnitude of the vector parameter in a switched manner for each arbitrary period of time.

8. The charged particle beam device according to claim 1, further comprising:
a monitor that displays an input screen on which a specific position on the specimen is selected in advance; and
a drive mechanism that moves the specimen stage such that the specific position on the specimen does not change in the images of transmitted charged particles before or after the vector parameter is changed.

9. The charged particle beam device according to claim 1, further comprising:
a monitor that displays an input screen on which a specific position on the specimen is selected in advance; and
an operation unit that adjusts a focal point and brightness such that the focal point and brightness at the specific position on the specimen do not change in the images of transmitted charged particles before or after the vector parameter is changed.

10. The charged particle beam device according to claim 1,
wherein the detector is a light-emitting member that emits light by charged particles which are transmitted through or scattered by the interior of the specimen.

11. The charged particle beam device according to claim 10,
wherein visible light, ultraviolet light, or infrared light in a specific or all wavelength regions is capable of passing through the light-emitting member.

12. The charged particle beam device according to claim 1,
wherein the specimen base is a specimen base that is used in common in an optical microscope device and in a charged particle microscope device.

13. The charged particle beam device according to claim 1,
wherein the detector is a semiconductor detecting element.

14. The charged particle beam device according to claim 1, further comprising:
a partition film that is attachable and detachable and allows the primary charged particle beam to be transmitted or to pass therethrough,
wherein the partition film separates the inner space of the charged particle optical lens tube from a space where the specimen is mounted.

15. A specimen observation method for observing a specimen by irradiation with a primary charged particle beam, the method comprising:
a step of obtaining an image of transmitted charged particles of the specimen by irradiation with the primary charged particle beam, the specimen being arranged either directly or through a predetermined member on a detector that detects charged particles which are transmitted through or scattered by the interior of the specimen;
a step of changing a vector parameter that defines the interrelationship between the primary charged particle beam and the specimen; and
a step of obtaining an image of transmitted charged particles of the specimen by irradiation with the primary charged particle beam with the changed vector parameter,
wherein, by irradiation with the primary charged particle beam with a plurality of different vector parameters, images of transmitted charged particles of the specimen that correspond to each of the vector parameters are obtained.

16. The specimen observation method according to claim 15,
wherein the vector parameter includes at least one of the relative angle between the direction of incidence of the primary charged particle beam and the specimen, the incident energy of the primary charged particle beam, and the amount of a current of the primary charged particle beam.

17. The specimen observation method according to claim 15, further comprising:
a step of displaying a plurality of images of transmitted charged particles corresponding to each of the vector parameters in order of magnitude of the vector parameter in a switched manner for each arbitrary period of time.

18. The specimen observation method according to claim 15,
wherein a substance in which a metal label is included is injected into the specimen, and
the image of transmitted charged particles of the specimen represents the position and density of the metal label that is specifically included in the specimen.

19. The specimen observation method according to claim 15, further comprising:
a step of obtaining an image of the specimen with an optical microscope; and
a step of arranging a desired position on the specimen at a position where irradiation is performed with the primary charged particle beam on the basis of the image obtained with the optical microscope.

20. The specimen observation method according to claim 19, further comprising:
a step of observing the specimen with a first optical microscope that is installed outside a charged particle beam device;
a step of specifying a position that is observed with the first optical microscope on the specimen with a second optical microscope that is installed inside the charged particle beam device; and
a step of obtaining an image of transmitted charged particles at the position, which is specified by the second optical microscope on the specimen, with a charged particle beam microscope that is installed inside the charged particle beam device.

21. The specimen observation method according to claim 19,
wherein the position on the specimen that is observed with the optical microscope is stored by a mark that is formed at a predetermined position on the detector or on a specimen base which is configured to include the detector.

22. The specimen observation method according to claim 15, further comprising:
a step of observing the three-dimensional internal structure of the interior of the specimen on the basis of a plurality of the images of transmitted charged particles that is obtained in correspondence with each of the vector parameters.

* * * * *